United States Patent
Wagner et al.

(10) Patent No.: US 7,183,392 B2
(45) Date of Patent: Feb. 27, 2007

(54) SITE-SPECIFIC, COVALENT BIOCONJUGATION OF PROTEINS

(75) Inventors: Peter Wagner, Belmont, CA (US); Lifu Ma, Castro Valley, CA (US); Steffen Nock, Redwood City, CA (US); David Wilson, Hayward, CA (US); Jens Sydor, Foster City, CA (US)

(73) Assignee: Zyomyx, Inc., Hayward, CA (US)

( * ) Notice: Subject to any disclaimer, the term of this patent is extended or adjusted under 35 U.S.C. 154(b) by 0 days.

(21) Appl. No.: 09/820,210

(22) Filed: Mar. 27, 2001

(65) Prior Publication Data

US 2002/0013003 A1 Jan. 31, 2002

Related U.S. Application Data

(60) Provisional application No. 60/235,955, filed on Sep. 26, 2000, provisional application No. 60/192,640, filed on Mar. 27, 2000.

(51) Int. Cl.
*C07K 17/06* (2006.01)
*C07K 1/13* (2006.01)

(52) U.S. Cl. ............... 530/391.5; 530/391.1; 530/391.3; 530/402

(58) Field of Classification Search ........... 530/402, 530/391.1, 391.3, 391.5; 436/531, 527, 532, 436/544, 545, 546
See application file for complete search history.

(56) References Cited

U.S. PATENT DOCUMENTS

| 5,444,150 | A | * | 8/1995 | Inman et al. |
| 5,532,379 | A | | 7/1996 | Fujimoto et al. |
| 5,601,824 | A | | 2/1997 | Hoess et al. |
| 5,840,712 | A | | 11/1998 | Morgan, Jr. et al. |
| 5,851,778 | A | * | 12/1998 | Oh et al. |

FOREIGN PATENT DOCUMENTS

| WO | WO00/02050 A | 1/2000 |
| WO | WO 00/04382 A1 | 1/2000 |

OTHER PUBLICATIONS

Roberts et al, Basic Principles of Organic Chemistry, Second edition. Menlo Park. W.A. Bejamin, Inc. (1977), 1208-1210.*

Boring, Daniel L. et al., "Trifunctional Agents as a Design Strategy for Tailoring Ligand Properties: Irreversible Inhibitors of $A_1$ Adenosine Receptors", *Bioconjugate Chem.*, 1991, pp. 77-88, vol. 2, No. 2, American Chemical Society.

Roberts, John D. et al., *Basic Principles of Organic Chemistry*, 1977, pp. 1208-1210, W.A. Benjamin, Inc., Menlo Park, California.

Boring, Daniel L., et al. "Trifunctional Agents as a Design Strategy for Tailoring Ligand Properties: Irreversible Inhibitors of $A_1$ Adenosine Receptors", *Bioconjugate Chemistry* (1991) 2(2)77-88.

Jacobson, Kenneth A., et al. "Cleavable Trifunctional' Approach to Receptor Affinity Labeling: Chemical Regeneration of Binding to $A_1$-Adenosine Receptors", *Bioconjugate Chemistry* (1995) 6(3):255-263.

Jacobson, Kenneth A., et al "Molecular Probes For Muscarinic Recepetors: Functionalized Congeners of Selective Muscarinic Antagonists", *Life Sciences* (1995) 56(11/12):823-830.

Ozaki, Shoichiro, et al. "Synthesis and biological properties of 2-substituted *myo*-inositol 1,4,5-trisphosphate analogues directed toward affinity chromatography and photoaffinity labeling", *Carbohydrate Research* (1992) 234(0):189-206.

Geselowitz, Daniel A., et al. "Quantitation of Triple-Helix Formation Using a Photo-Cross-Linkable Aryl Azide/Biotin/Oligonucleotide Conjugate", *Bioconjugate Chemistry* (1995) 6(4):502-506.

\* cited by examiner

*Primary Examiner*—Mary E. Ceperley
(74) *Attorney, Agent, or Firm*—Townsend and Townsend and Crew LLP

(57) ABSTRACT

Heterofunctional crosslinking groups are provided having the formula:

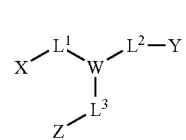

(I)

wherein W is a covalent core component; $L^1$, $L^2$ and $L^3$ are independently linking groups; X is a non-covalent or reversibly covalent protein tag binder; Y is a activatable covalent linking group; and Z is a protected or unprotected covalent crosslinking group.

5 Claims, 5 Drawing Sheets

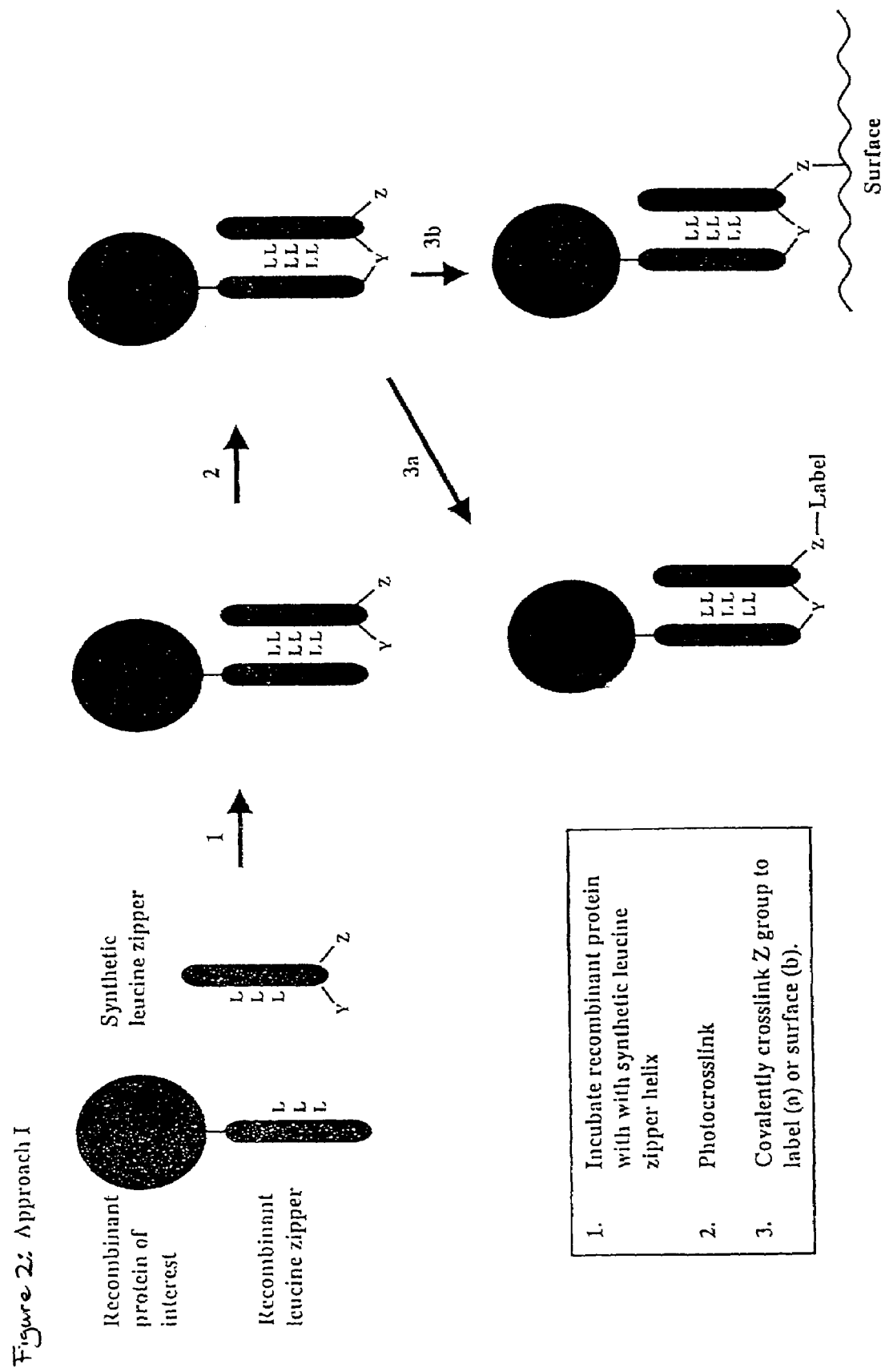

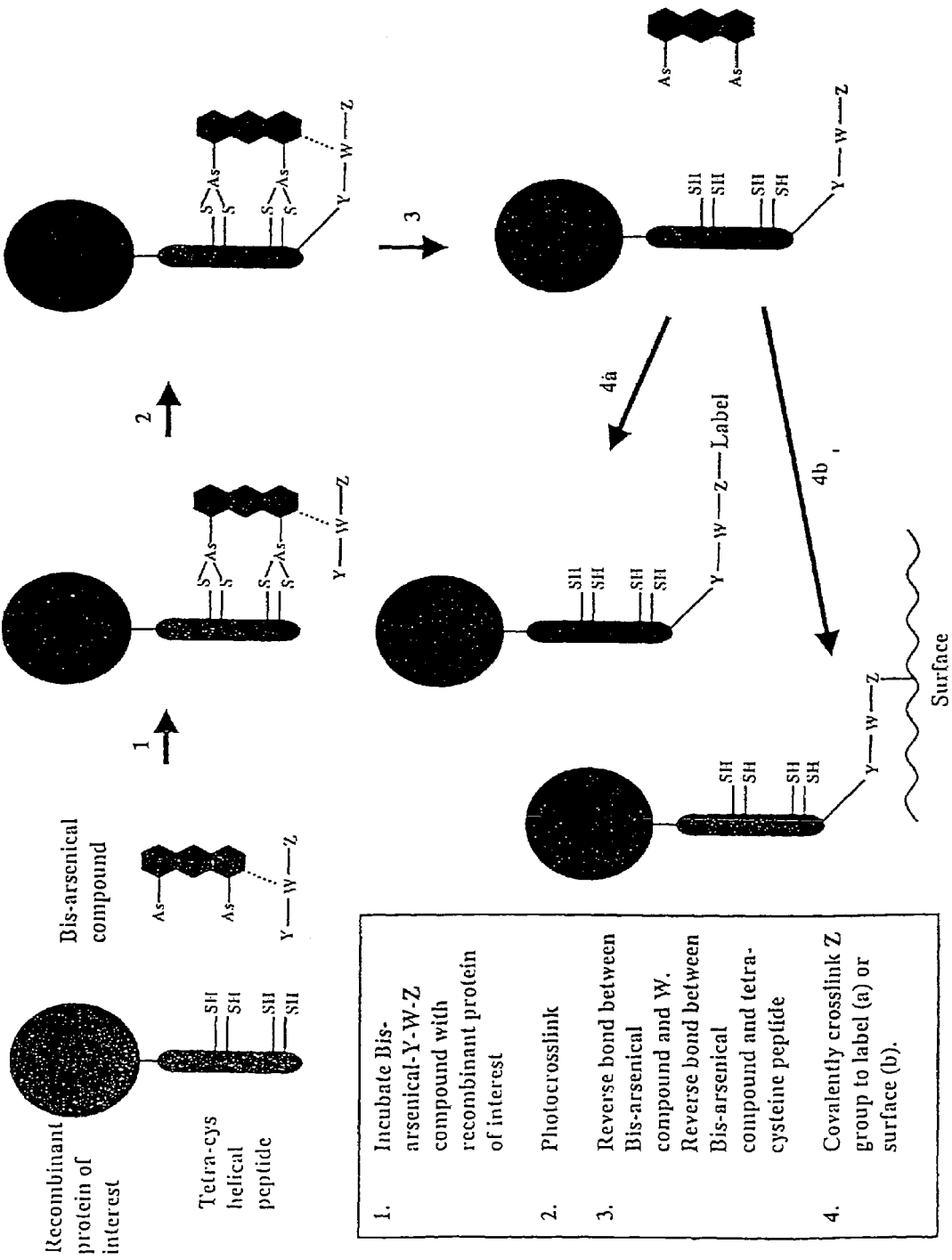

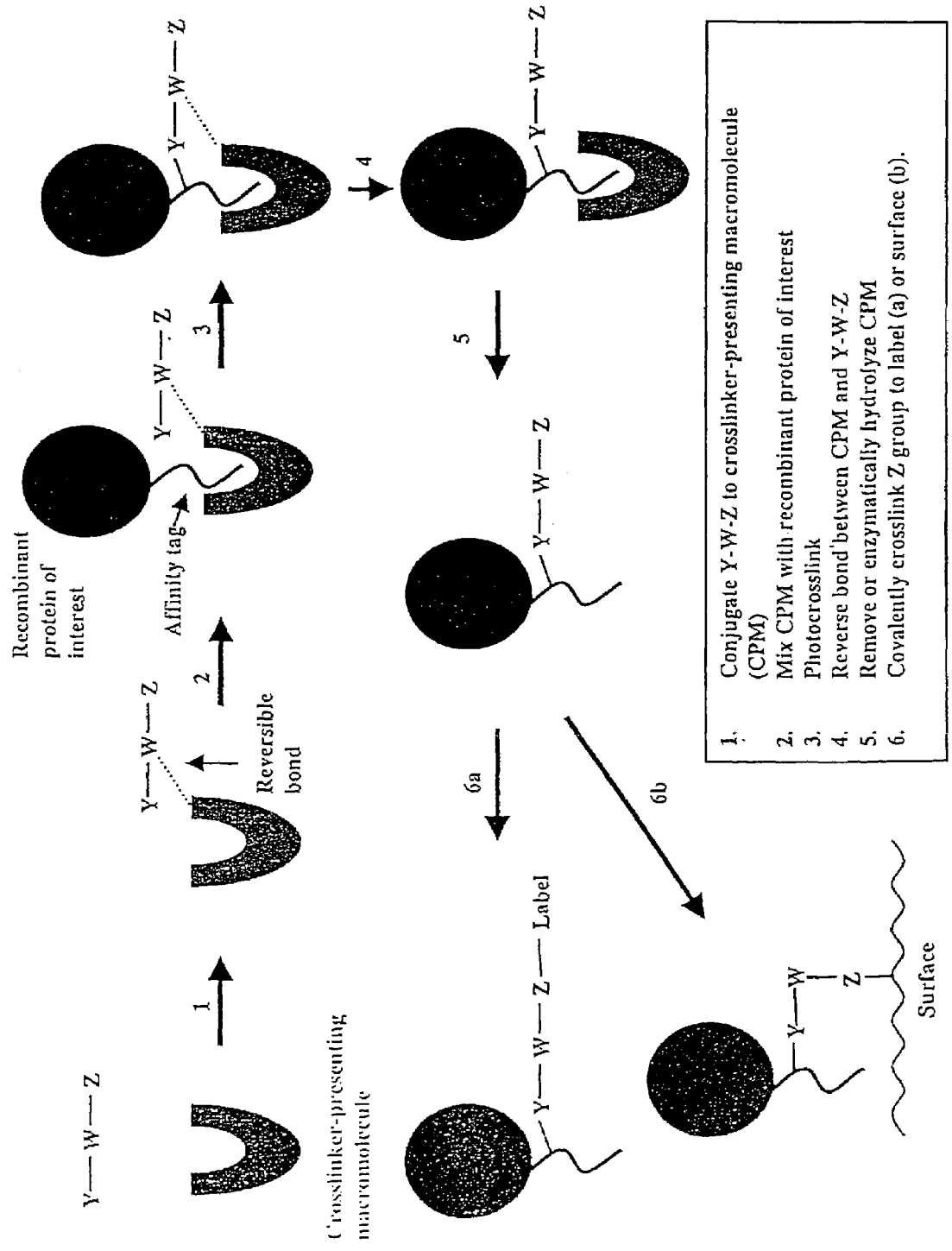
Figure 4a: Approach III

Examples of systems for delivering crosslinker to recombinant proteins

| System: | Tat/TAR | aptamer | DNA-binding | PDZ | calmodulin | coiled coil |
|---|---|---|---|---|---|---|
| Affinity tag: | Tat | subst P | homeo-domain | PDZ-binding peptide | calmodulin-binding peptide | leucine zipper peptide |
| Crosslinker-presenting macromol: | TAR | aptamer | DNA | PDZ domain | calmodulin | leucine zipper peptide |

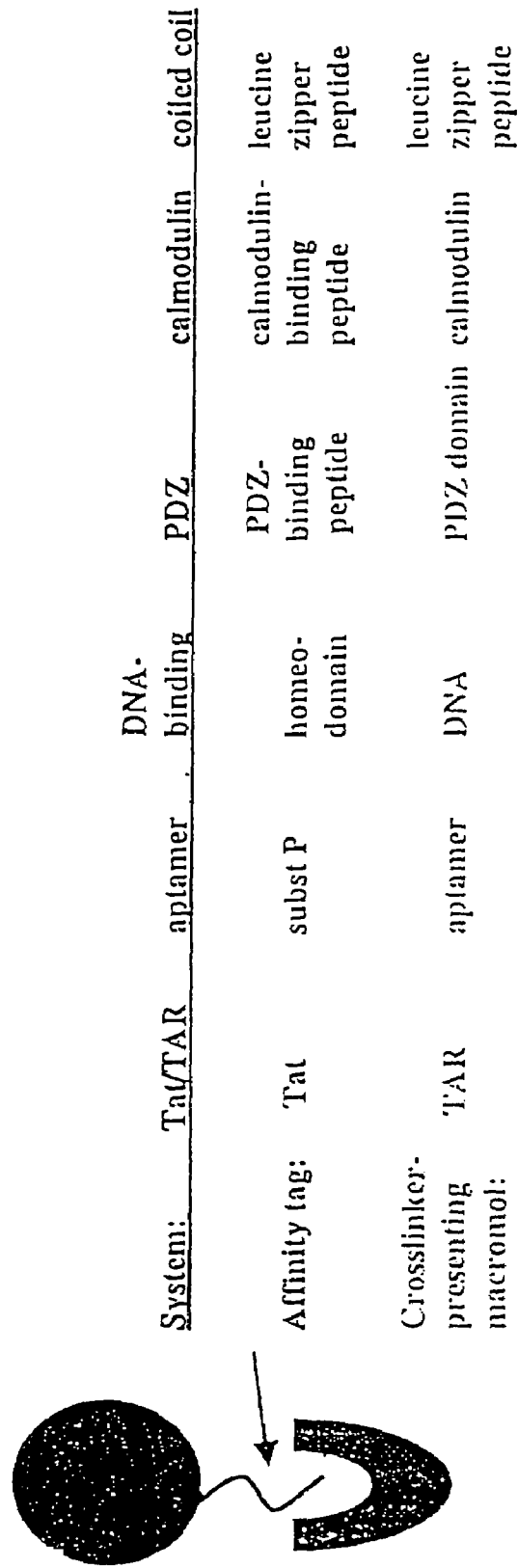

Figure 4b Approach III continued

SITE-SPECIFIC, COVALENT BIOCONJUGATION OF PROTEINS

CROSS-REFERENCES TO RELATED APPLICATIONS

This application claims the benefit of provisional applications Ser. Nos. 60/192,640, filed Mar. 27, 2000 and 60/235,955, filed Sep. 26, 2000, the disclosures of which are incorporated herein by reference.

STATEMENT AS TO RIGHTS TO INVENTIONS MADE UNDER FEDERALLY SPONSORED RESEARCH AND DEVELOPMENT

Not applicable

FIELD OF THE INVENTION

The present invention provides compositions and methods which are useful for site-specifically modifying a protein or proteins. Accordingly, the compositions and methods can be used to introduce, for example, a label to a known location in a protein or for attaching a protein to a solid support wherein the point of attachment is made at a known location of the protein.

BACKGROUND OF THE INVENTION

Support-bound proteins are finding increasing utility, for example, in the search for small molecule modulators of the proteins in drug discovery programs. Recently, protein arrays have been described for high-throughput screening (see co-pending application Ser. No. 09/115,455, filed Jul. 14, 1998; Ser. No. 09/353,215, filed Jul. 14, 1999 and Ser. No. 09/353,555, filed Jul. 14, 1999; and related PCT published applications WO 00/04382, 00/04389 and 00/04390).

Applications Ser. Nos. 09/353,215 and 09/353,555 describe a number of hurdles that must be overcome to provide protein arrays of high quality which produce accurate and reproducible screening results. Typically, proteins must remain hydrated, be kept at ambient temperatures, and are very sensitive to the physical and chemical properties of the support materials. Thus, maintaining protein activity at the liquid-solid interface requires new immobilization strategies which address the sensitivity of the proteins to the environment and further can orient the protein in a manner which ensures accessibility of the protein active site to potentially interacting molecules.

The present invention addresses these and other considerations in the preparation and use of protein arrays.

SUMMARY OF THE INVENTION

The present invention provides a variety of crosslinking reagents, labeling reagents, solid supports, modified proteins, labeled or support-bound proteins, and arrays of proteins. In general, these reagents and compositions are useful in the characterization of protein-protein, protein-nucleic acid, protein-drug, and protein-ligand interactions.

In one aspect, the present invention provides a heterofunctional crosslinking reagent, preferably having the formula:

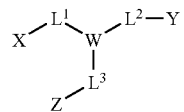
(I)

wherein W is a covalent linking core, preferably a trivalent core; $L^1$, $L^2$ and $L^3$ are independently linking groups; X is a specific protein tag binder which binds a protein at a specific region or regions within the protein, preferably reversibly covalently, non-covalently, or covalently; Y is an activatable, preferably photoactivatable, covalent crosslinking group adapted to link the heterofunctional crosslinker covalently at or adjacent the specific region or regions of the protein; and Z is a covalent crosslinking group, preferably a protected or unprotected covalent crosslinking group.

In another aspect, the present invention provides a crosslinking reagent preferably having the formula:

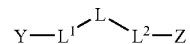
(II)

wherein L is a helical, preferably an α-helical, component of a leucine zipper; $L^1$ and $L^2$ are each independently selected from the group consisting of a bond and a linking group; Y is a activatable, preferably a photoactivatable crosslinking group; and Z is a protected or unprotected chemical crosslinking group. In certain embodiments, L will be linked to $L^1$ and $L^2$ via covalent core W, yet in other embodiments, $L^1$ will be linked to $L^2$ through L.

In yet another aspect, the present invention provides protein labeling reagents preferably having the formula:

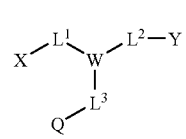
(III)

wherein W is a covalent core, preferably a covalent core component; $L^1$, $L^2$ and $L^3$ are each independently linking groups; X is a reversibly covalent or non-covalent protein tag binder; Y is an activatable, preferably photoactivatable, covalent crosslinking group; and Q is a label or a reporter group.

In a related aspect, the present invention provides protein labeling reagents preferably having the formula:

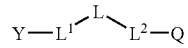
(IV)

wherein L is a helical component of a leucine zipper; $L^1$ and $L^2$ are each independently a bond or a linking group; Y is an activatable, preferably a photoactivatable, covalent crosslinking group; and Q is a label or a reporter group. In certain embodiments, $L^1$ and $L^2$ may be covalently linked to L via a covalent core. In other embodiments, $L^1$ may be linked to $L^2$ through L.

In still another aspect, the present invention provides a protein conjugate preferably having the formula:

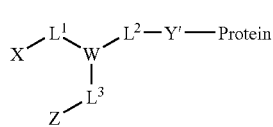
(V)

wherein W is a covalent, preferably trivalent, core component; $L^1$ is a linking group (or the vestige of a linking group following removal of a protein tag binder, e.g., X is H); $L^2$ and $L^3$ are each independently a bond or a linking group; X is a hydrogen or a non-covalent protein tag binder; Y' is an activatable, preferably a photoactivatable crosslinking group that has been activated and covalently attached to a protein; and Z is a protected or unprotected covalent crosslinking group.

In yet another and related aspect, the present invention provides a protein composition preferably having the formula:

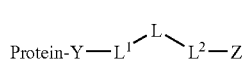
(VI)

wherein L is a helical component, preferably an α-helical component, of a leucine zipper; $L^1$ and $L^2$ are each independently a bond or a linking group; Y is an activatable, preferably photoactivatable, crosslinking group that has been activated and covalently attached at or adjacent a specific selected region of a protein; and Z is a protected or unprotected chemical crosslinking group.

In yet another aspect, the present invention provides protein compositions comprising a protein and a crosslinking reagent that is attached to either a label or a solid support. In one group of embodiments, in preferred embodiments, the conjugates has the formula:

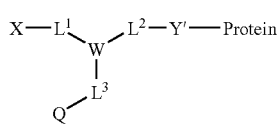
(VII)

wherein, the symbols W, X, $L^1$, $L^2$ and $L^3$ are as described above, Y' now represents the residue of an activatable, preferably photo activatable covalent crosslinking group (Y in the compounds of formula I) after formation of a covalent linkage to the protein, and Q is a label or a solid support.

In a related aspect, the present invention provides a protein composition preferably having the formula:

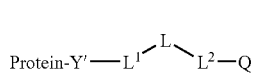
(VIII)

wherein L is an α-helical component of a leucine zipper; $L^1$ and $L^2$ are each independently selected from a bond and a linking group; Y' is a photoactivatable crosslinking group that has been activated and covalently attached to a protein; and Q is a solid support or a label.

In yet another aspect, the present invention provides a supports-bound crosslinking reagent, having the formula:

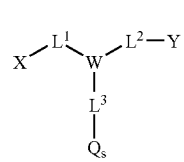
(IX)

wherein W is a covalent core component; $L^1$ is a cleavable or non-cleavable linking group; $L^2$ and $L^3$ are each independently a bond or a linking group; X is a reversibly covalent or non-covalent protein tag binder; Y is a photoactivatable covalent crosslinking group; and $Q_s$ is a solid support, a monolayer attached to a support, or a thinfilm attached to a support.

In a related aspect, the invention farther provides a support-bound crosslinking composition having the formula:

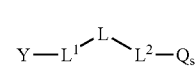
(X)

wherein L is an α-helical component of a leucine zipper; $L^1$ and $L^2$ are each independently a bond or a linking group; Y is a photoactivatable crosslinking group; and $Q_s$ is a member selected from a solid support, a monolayer attached to a support and a thinfilm attached to a support.

In addition to the reagents, conjugates and compositions provided herein, the present invention provides a number of methods that are generally directed to the use of the subject reagents, conjugates and compositions (e.g., methods for labeling proteins, methods for attaching proteins to supports, and the like). Still further, the present invention provides protein arrays in which the proteins are attached to a support using the crosslinking reagents described herein.

Accordingly, in another aspect, the present invention provides an array of proteins, comprising:
(a) a substrate;
(b) at least one organic thinfilm on at least a portion of the substrate surface; and
(c) a plurality of patches arranged in discrete, known regions on portions of the substrate surface covered by the organic thinfilm, wherein each of the patches comprises a protein immobilized on the underlying organic thinfilm using a heterofunctional crosslinking agent or a leucine zipper crosslinking reagent. Preferably, the heterofunctional crosslinking agent used is a compound of formula I. Alternatively, the leucine zipper crosslinking reagent is a compound of formula II.

In another aspect, the present invention provides a method for attaching a protein to a solid support, the method comprising:

(i) forming a reversibly covalent or non-covalent association between a protein tag present in the protein and a protein tag binder of a heterofunctional linking group;

(ii) forming a covalent linkage between the solid support and a first functional group of the heterofunctional linking group; and (iii) forming a covalent linkage between the protein and a second functional group of the heterofunctional linking group.

In the method above, the steps of forming a covalent linkage between the solid support and the first functional group (step ii) and forming a covalent linkage between the protein and a second functional group (step iii) can be performed either with step ii prior to step iii or in the reverse order. Additionally, in some embodiments, the method provides for the site-specific attachment of the protein to the support in order to properly orient the protein for potential interactions. Preferably, the heterofunctional linking group is a linking group of formula I.

In yet another aspect, the present invention provides a method for attaching a protein to a heterofunctional crosslinking reagent having an available functionalized linker arm, said method comprising:

(i) forming a reversibly covalent or non-covalent association between said protein and a protein tag binder present on a hetero functional crosslinking reagent;

(ii) forming a covalent linkage between said protein and a first reactive functional group of said heterofunctional crosslinking reagent, to provide a protein having a covalently attached heterofunctional crosslinking reagent having an available functionalized linker arm.

In another aspect, the present invention provides a method for covalently attaching a heterofunctional crosslinking reagent to a recombinant protein having an engineered helical portion, the method comprising:

(i) forming a non-covalent association complex between the engineered helical portion of the recombinant protein and a heterofunctional crosslinking reagent comprising a peptide helical portion, a photocrosslinking portion and a chemical crosslinking portion that is unreactive to functional groups normally present on a protein; and (ii) activating the non-covalent association complex to form a covalent linkage between the recombinant protein and the photocrosslinking group of the heterofunctional crosslinking reagent.

In yet another aspect, the present invention provides a method for attaching a crosslinking reagent to a recombinant protein having an engineered peptide portion comprising at least four cysteine residues, said method comprising:

(i) forming a covalent complex between the engineered peptide portion of the recombinant protein and a heterofunctional crosslinking reagent, wherein the heterofunctional crosslinking reagent comprises an organoarsenical group reactive with the at least four cysteine residues present in the engineered helical peptide portion, a photocrosslinking portion and a chemical crosslinking portion that is unreactive to functional groups normally present on a protein;

(ii) activating the covalent complex to form a covalent linkage between the recombinant protein and the photocrosslinking group of the heterofunctional crosslinking reagent; and (iii) releasing the organoarsenical group from the protein and the crosslinking reagent to provide a recombinant protein having an attached crosslinking reagent.

In yet another aspect, the present invention provides a method for attaching a crosslinking reagent to a recombinant protein having an affinity tag, the method comprising:

(i) forming a non-covalent association complex between the recombinant protein affinity tag and a heterofunctional crosslinking reagent, wherein the heterofunctional crosslinking reagent comprises a presenting macromolecule portion specific for the affinity tag and attached to the remainder of the heterofunctional crosslinking reagent via a cleavable linking group, a photocrosslinking portion and a protected or unprotected chemical crosslinking portion that is unreactive to functional groups normally present on a protein;

(ii) illuminating the non-covalent association complex to form a covalent linkage between the recombinant protein and the photocrosslinking group of the heterofunctional crosslinking reagent; and (iii) releasing the presenting macromolecule portion from the affinity tag and from the heterofunctional crosslinking reagent to provide a recombinant protein having an attached reactive functional group.

In still other aspects, the present invention provides labeled proteins as well as solid support-bound proteins that are prepared using the crosslinking reagents or methods described above.

In other aspects, the present invention provides methods of screening a plurality of proteins to identify compounds which interact with at least one of the proteins.

Another aspect of the invention includes a method for covalently linking a protein to a compound, biological moiety, or substrate within one or more specific regions of the protein, the method comprising the steps of:

i) providing a heterofunctional crosslinker comprising;
  a) one or more first functional groups capable of reversibly covalently or non-covalently crosslinking specifically at one or more first functional group sites within at least one of the one or more specific regions of the protein,
  b) one or more second functional groups capable of selectively covalently crosslinking to the protein at or adjacent the first functional group sites when activated under selectively activating conditions,
  c) one or more third functional groups capable of covalently attaching, chemisorbing, or physisorbing to the compound, biological moiety, or substrate, and,
  d) a covalent core for covalently linking the first, second, and third groups together to form the heterofunctional crosslinking reagent to covalently link the protein, through the heterofunctional crosslinker's covalent core to the compound, biological moiety, or substrate;

ii) crosslinking at least one of the one or more first functional groups to at least one of the one or more first functional group sites within the one or more specific regions of the protein;

iii) selectively crosslinking at least one of the one or more second functional groups within the specific regions of the protein by selectively activating the second functional groups; and, iv) selectively crosslinking at least one of the one or more third functional groups to the compound, biological moiety, or substrate;

wherein the protein is covalently linked to the compound, biological moiety, or substrate through the covalent core of the hetereofunctional crosslinker.

Certain embodiments may have steps (ii) (iii) and (iv) switched in order as (i) then (iv) then (ii) then (iii), may have at least one of the one or more second functional groups is selected from the group consisting of a biotin, a leucine zipper, a monomer unit of a coiled-coil dimer, a fragment of an antibody, a chelatable metal, and an aptamer, may have at least one of the one or more second functional groups also functions as the covalent core to covalently link at least one of the first functional groups and at least one of the second functional groups together, and may have at least one of the one or more second functional groups is a photocrosslinker, and the selectively activating is selectively exposing the second functional group photocrosslinker to a photon source.

Another aspect of the invention provides for a heterofunctional crosslinker for covalently linking a protein to a compound, biological moiety, or substrate within one or more specific regions of the protein, the heterofunctional crosslinker comprising i) one or more first functional groups capable of reversibly covalently or non-covalently crosslinking specifically at one or more first functional group sites within at least one of the one or more specific regions of the protein, ii) one or more second functional groups capable of selectively covalently crosslinking to the protein at or adjacent the first functional group sites when activated under selectively activating conditions, iii) one or more third functional groups capable of covalently attaching, chemisorbing, or physisorbing to the compound, biological moiety, or substrate, and, iv) a covalent core for covalently linking the first, second, and third groups together to form the heterofunctional crosslinking reagent to covalently link the protein, through the heterofunctional crosslinker's covalent core to the compound, biological moiety, or substrate;

wherein the heterofunctional crosslinker is adapted to covalently link the protein to the compound, biological moiety, or substrate through the covalent core of the hetereofunctional crosslinker when at least one of the one or more second functional groups is attached to the protein within at least one of the one or more specific regions, and at least one of the third functional groups is attached to the compound, biological moiety, or substrate. Certain embodiments of the heterofunctional crosslinker may include having at least one of the one or more second functional groups is selected from the group consisting of a biotin, a leucine zipper, a monomer unit of a coiled-coil dimer, a fragment of an antibody, a chelatable metal, and an aptamer, may include having at least one of the one or more second functional groups also function as the covalent core to covalently link at least one of the first functional groups and at least one of the second functional groups together, may include having at least one of the one or more second functional groups also function as the covalent core to covalently link at least one of the first functional groups and at least one of the second functional groups together, and may include having at least one of the one or more second functional groups be a photocrosslinker, and the selective activation be selective exposure of the second functional group photocrosslinker to a photon source.

BRIEF DESCRIPTION OF THE DRAWINGS

FIG. 2 depicts the use of a leucine zipper to covalently modify a protein for attachment to either a label or a surface.

FIG. 3 depicts the use of a an organoarsenical reagent and a modified protein having a tetra-cysteine helical peptide to covalently modify the protein for attachment to either a label or a surface.

FIG. 4 depicts the crosslinker-presenting macromolecule approach to attaching a protein to either a label or a surface.

DESCRIPTION OF THE INVENTION

Abbreviations and Definitions

Definitions

Figure 1:
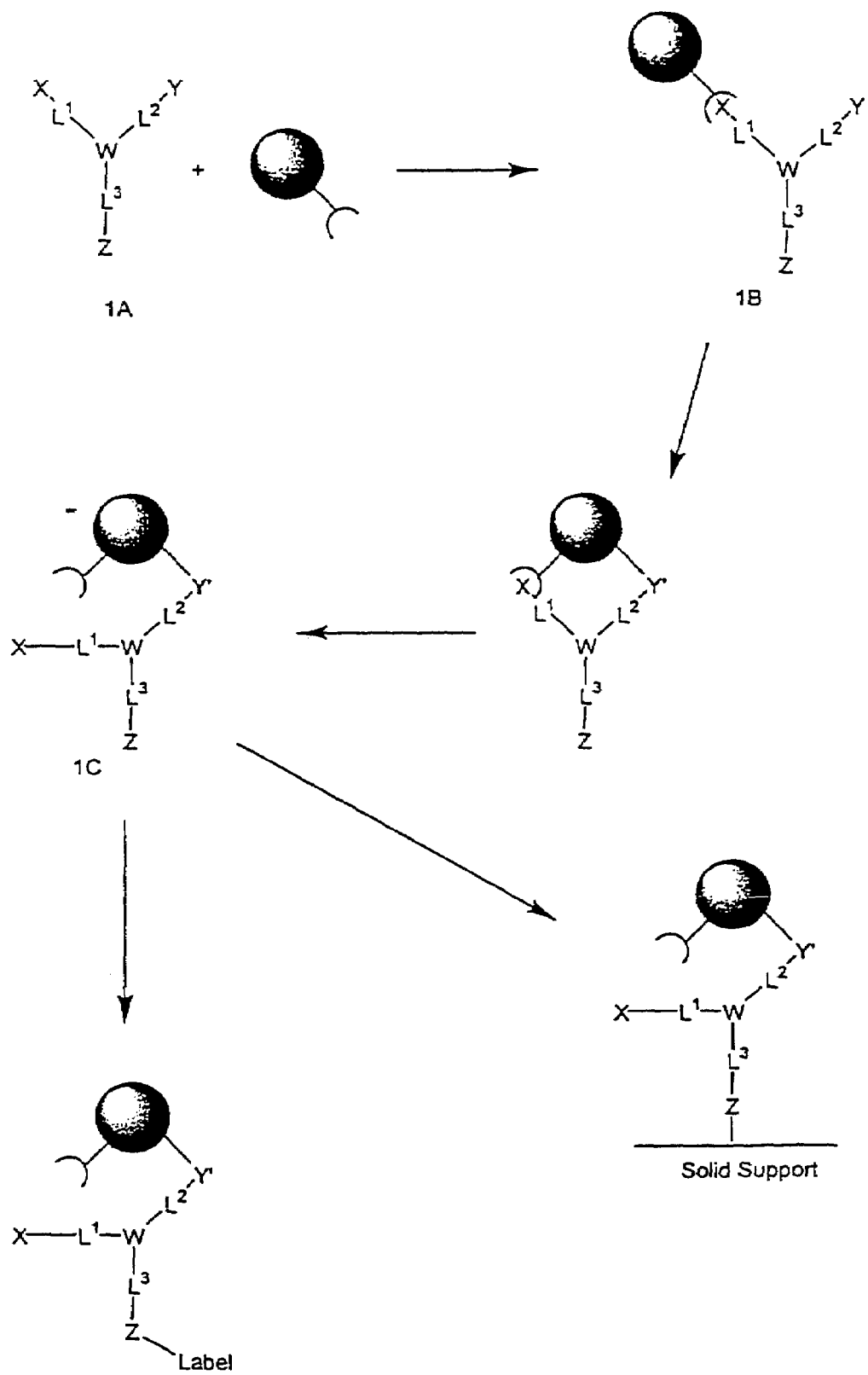
FIG. 1 illustrates a heterofunctional crosslinking group and its use in attaching a protein to a label or surface.

As used herein, the term "protein" means a polymer of amino acid residues linked together by peptide bonds. The term is meant to include proteins, polypeptides, and peptides of any size, structure, or function. Typically, however, a protein will be at least six amino acids long. Preferably, if the protein is a short peptide, it will be at least about 10 amino acid residues long. A protein may be naturally occurring, recombinant, or synthetic, or any combination of these. A protein may also be just a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid. An amino acid polymer in which one or more amino acid residues is an "unnatural" amino acid, not corresponding to any naturally occurring amino acid, is also encompassed by the use of the term "protein" herein.

A "fragment of a protein" means a protein which is a portion of another protein. For instance, fragments of a protein may be polypeptides obtained by digesting a full-length protein isolated from cultured cells. A fragment of a protein will typically comprise at least six amino acids. More typically, the fragment will comprise at least ten amino acids. Preferably, the fragment comprises at least about 16 amino acids.

The term "antibody" means an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term "antibody fragment" refers to any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the $NH_2$-terminal domain. The polypeptide linker may be of variable length and composition so long as the two variable domains are bridged without serious steric interference. Typically, the linkers are comprised primarily of stretches of glycine and seine residues with some glutamic acid or lysine residues interspersed for solubility.

An "Fv" fragment is an antibody fragment which consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

A "F(ab')$_2$" fragment is an antibody fragment essentially equivalent to that obtained from immunoglobulins (typically IgG) by digestion with an enzyme pepsin at pH 4.0–4.5. The fragment may be recombinantly produced.

A "Fab" fragment is an antibody fragment essentially equivalent to that obtained by reduction of the disulfide bridge or bridges joining the two heavy chain pieces in the F(ab')$_2$ fragment. The Fab' fragment may be recombinantly produced.

A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

The term "protein tag binder" means a molecule or a multi-molecular complex that can bind to a protein or an appendage of a protein. Protein tag binders preferably bind their binding partners in a substantially specific manner. Protein tag binders having a dissociation constant ($K_D$) of less than about $10^{-6}$ M are preferred. Antibodies or antibody fragments are highly suitable as protein tag binders. Antigens may also serve as protein tag binders as they are capable of binding antibodies. A receptor which binds a protein ligand is another example of a possible protein tag binder. Protein tag binders as used herein are understood to be limited to agents which only interact with their binding partners through non-covalent, reversibly covalent, or weakly covalent interactions. Certain embodiments include using a protein-tag binder which is introduced to a specific site within a target protein by an exogenous mediator such as Bir A enzyme specifically introducing a component such as biotin to a specific site or sites within a protein, where the biotin in covalently included into a heterofunctional croslinker which later is covalently linked to or adjacent the specific site or sites of the protein.

The term "protein tag" or "binding partner" means that portion of a protein which is bound by a particular protein tag binder, preferably in a substantially specific manner. In some cases, the binding partner or tag may be the protein normally bound in vivo by a protein that is a protein tag binder (e.g., antibody-antigen binding pairs). Additionally, the protein tag or binding partner may be the protein or peptide on which the protein tag binder was selected (through in vitro or in vivo selection) or raised (as in the case of antibodies). A binding partner may be shared by more than one protein tag binder. For instance, a binding partner which is bound by a variety of polyclonal antibodies may bear a number of different epitopes. One protein tag binder may also bind to a multitude of binding partners (for instance, if the binding partners share the same epitope). In view of the above, the terms "protein tag" and "protein tag binder" is meant to include, but not be limited to, those pairs such as fusion tags/tag binders, protein/ligand, enzyme/substrate, antibody/antigen, peptide/peptide or epitope, an epitope or region and a material, atom, or ion such as poly His to Ni.

"Conditions suitable for protein binding" means those conditions (in terms of salt concentration, pH, detergent, protein concentration, temperature, etc.) which allow for binding to occur between a protein and its binding partner in solution. Preferably, the conditions are not so lenient that a significant amount of nonspecific protein binding occurs.

As used herein, the term "array" refers to an arrangement of entities in a pattern on a substrate. Although the pattern is typically a two-dimensional pattern, the pattern may also be a three-dimensional pattern. The term "substrate" refers to the bulk, underlying, and core material of the arrays of the invention.

The term "coating" means a layer that is either naturally or synthetically formed on or applied to the surface of the substrate. For instance, exposure of a substrate, such as silicon, to air results in oxidation of the exposed surface. In the case of a substrate made of silicon, a silicon oxide coating is formed on the surface upon exposure to air. In other instances, the coating is not derived from the substrate and may be placed upon the surface via mechanical, physical, electrical, or chemical means. An example of this type of coating would be a metal coating that is applied to a silicon or polymer substrate or a silicon nitride coating that is applied to a silicon substrate. Although a coating may be of any thickness, typically the coating has a thickness smaller than that of the substrate.

An "interlayer" is an additional coating or layer that is positioned between the first coating and the substrate. Multiple interlayers may optionally be used together. The primary purpose of a typical interlayer is to aid adhesion between the first coating and the substrate. One such example is the use of a titanium or chromium interlayer to help adhere a gold coating to a silicon or glass surface. However, other possible functions of an interlayer are also anticipated. For instance, some interlayers may perform a role in the detection system of the array (such as a semiconductor or metal layer between a nonconductive substrate and a nonconductive coating).

An "organic thinfilm" is a thin layer of organic molecules which has been applied to a substrate or to a coating on a substrate if present. Typically, an organic thinfilm is less than about 20 nm thick. Optionally, an organic thinfilm may be less than about 10 nm thick. An organic thinfilm may be disordered or ordered. For instance, an organic thinfilm can be amorphous (such as a chemisorbed or spin-coated polymer) or highly organized (such as a Langmuir-Blodgett film or self-assembled monolayer). An organic thinfilm may be heterogeneous or homogeneous. Organic thinfilms which are monolayers are preferred. A lipid bilayer or monolayer is a preferred organic thinfilm. Optionally, the organic thinfilm may comprise a combination of more than one form of organic thinfilm. For instance, an organic thinfilm may comprise a lipid bilayer on top of a self-assembled monolayer. A hydrogel may also compose an organic thinfilm. The organic thinfilm will typically have functionalities exposed on its surface which serve to enhance the surface conditions of a substrate or the coating on a substrate in any of a number of ways. For instance, exposed functionalities of the organic thinfilm are typically useful in the binding or covalent immobilization of the proteins to the patches of the array. Alternatively, the organic thinfilm may bear functional groups (such as polyethylene glycol (PEG)) which reduce the non-specific binding of molecules to the surface. Other exposed functionalities serve to tether the thinfilm to the surface of the substrate or the coating. Particular functionalities of the organic thinfilm may also be designed to enable certain detection techniques to be used with the surface. Alternatively, the organic thinfilm may serve the purpose of preventing inactivation of a protein immobilized on a patch of the array or analytes which are proteins from occurring upon contact with the surface of a substrate or a coating on the surface of a substrate.

A "monolayer" is a single-molecule thick organic thinfilm. A monolayer may be disordered or ordered. A monolayer may optionally be a polymeric compound, such as a polynonionic polymer, a polyionic polymer, or a blockcopolymer. For instance, the monolayer may be composed of a poly(amino acid) such as polylysine. A monolayer which is a self-assembled monolayer, however, is most preferred. One face of the self-assembled monolayer is typically composed of chemical flnctionalities on the termini of the organic molecules that are chemisorbed or physisorbed onto the surface of the substrate or, if present, the coating on the substrate. Examples of suitable functionalities of monolayers include the positively charged amino groups of poly-L-lysine for use on negatively charged surfaces and thiols for use on gold surfaces. Typically, the other face of the self-assembled monolayer is exposed and may bear any number of chemical functionalities (end groups). Preferably, the molecules of the self-assembled monolayer are highly ordered.

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

A "biological moiety" includes, but is not limited to, intact or portions of proteins, peptides including self-replicating peptides, amino acids, nucleic acids including nucleic acid monomers, oligonucleotides, polynucleotides, DNA from all sources, RNA, mRNA, tRNA, rRNA, vRNA, viral particles and components thereof, cells from sources including mammalian, bacterial, yeast and fungi, algae, and plants, which can be chemically derivatized by the second functional groups (Y) of the present invention.

A "first functional group" includes molecules and materials such as metal atoms and ions capable of selectively binding to a binding partner as described herein.

A "second functional group" includes functional groups capable of selectively forming covalent bonds with at least one of certain features of a biological moiety when exposed to an activating source or environment as described herein, for example, photocrosslinkers and photoactivation.

A "third functional group" includes groups capable of forming a covalent bond with at least one of certain compounds, biological moieties, or a substrate as described herein.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 to 24 carbon atoms being preferred in the present invention. A "lower alkyl" or "lower alkylene" is a shorter chain alkyl or alkylene group, generally having eight or fewer carbon atoms, preferably four or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, -Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. The term "heteroalkylene" by itself or as part of another substituent means a divalent radical derived from heteroalkyl, as exemplified by —$CH_2$—$CH_2$—S—$CH_2CH_2$— and —$CH_2$— S—$CH_2$—$CH_2$— NH—$CH_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "halo" or "halogen," by themselves or as part of another substituent, mean, unless otherwise stated, a fluorine, chlorine, bromine, or iodine atom.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The term "heteroaryl" refers to those aryl groups in which at least one of the rings contains from one to four heteroatoms selected from N, O, and S, wherein the nitrogen and sulfur atoms are optionally oxidized, and the nitrogen atom(s) are optionally quaternized. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 2-pyridyl, 2-pyrimidyl, 5-benzothiazolyl, purinyl, 2-benzimidazolyl, 5-indolyl, 1-isoquinolyl, 2-quinoxalinyl, 3-quinolyl, and the like. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene and heteroalkylene) can be a variety of groups selected from: —OR', =O, =NR', =N—OR', —NR'R", —SR', -halogen, —SiR'R"R'", —OC(O)R', —CO$_2$R', —CONR'R", —OC(O)NR'R", —NR"C(O)R', —NR"C(O)NR'R'", —NR"C(0)$_2$R', —NHC(NH$_2$)=NH, —NR"C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. Preferably, substituted alkyl groups will have from one to six independently selected substituents, more preferably from one to four independently selected substituents, most preferably from one to three independently selected substituents. In the substituents listed above, R', R" and R'" each independently refer to hydrogen, unsubstituted($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R'and R"are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NR'"C(O)NR'R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R' and R" are independently selected from hydrogen, ($C_1$–$C_8$)alkyl and heteroalkyl, unsubstituted aryl, (unsubstituted aryl)-($C_1$–$C_4$)alkyl, and (unsubstituted aryl)oxy-($C_1$–$C_4$)alkyl. Preferably, substituted aryl groups will have from one to four independently selected substituents, more preferably from one to three independently selected substituents, most preferably from one to two independently selected substituents.

As used herein, the term "heteroatom" is meant to include oxygen (O), nitrogen (N), sulfur (S), boron (B) and silicon (Si).

An "activatable crosslinking group" is a functional group that may be selectively activated by exposure to an activating agent, for example, light, acid or base, photo-initiated acid or base.

"Reversibly covalent bond" means a covalent bond that may transiently form between a protein and a protein tag group, for example a cysteine-cysteine disulfide bond. Such reversible covalent bonds typically break during assay or conditions used, by enzyme or other thermodynamic actions.

"Support substrates" are supports for immobilizing, and/or identifying a compound attached thereto, include porous, and preferably solid supports.

"Hetero functional crosslinker" is a compound having one or more first functional groups for selectively binding to one or more specific sites on a selected protein or other biological sample. Preferred embodiments include, bi-functional, trifunctional, tetrafunctional, pentafunctional, hexafunctional crosslinkers wherein at least one crosslinker group is capable of specifically binding to a specific region or regions on a protein, and a second covalent crosslinking functional group for forming a covalent linkage between the protein and the heterofunctional crosslinker at or adjacent the first functional group binding site, wherein the first functional group limits the area on or within the protein for which the second functional group may contact and form a covalent bond with the protein. In certain embodiments, the first functional group is specifically introduced to its corresponding site by an exogenous moiety, for example, a biotin containing heterofunctional crosslinker may be used by having the protein include a Bir A peptide sequence, and using free solution Bir A enzyme to attach the biotin containing heterofunctional crosslinker to the protein through the biotin, then later through the covalent linkage. In preferred embodiments, the second covalent linkage is stronger than the first.

General

The ability of a protein to bind site-specifically to another protein or peptide is essential for most cellular processes. To study very large macromolecular complexes, it would be useful to be able to incorporate probe molecules, such as fluorescent tags or photoactivatable crosslinkers, into specific sites on proteins. The development of covalent-bound probe molecules will allow the interaction of a particular component of a complex to be studied in a complicated background, such as in crude lysates or in living cells.

Most cross-linking reagents are based on the reactivity of a specific functional group found in an amino acid side chain. For example, the most commonly targeted amino acids contain side chains with nucleophilic functionalities that react with an electrophilic crosslinking reagent. However, the regiochemistry of these protein modification reactions shows little selectivity and often leads to multiply crosslinked products that are difficult to characterize. As a result, the extraction of information on the particular factor under investigation can be problematic.

One solution to this problem is to specifically attach a crosslinking reagent to a protein of interest by an affinity tag which is present in, for example, an engineered fusion protein at either termini or along the protein chain. A reactive moiety on the crosslinking agent can then be site-specifically attached to a known portion of a protein. In particular, a photoactivatable group can generate reactive species in situ, such as carbenes and nitrenes, that react rapidly with proteins in the immediate vicinity, irrespective of their amino acid sequence.

In view of the above need for new reagents, the present invention provides, in one aspect, new compounds which are useful for the site-specific introduction of a label to a protein, or for the site-specific immobilization of a protein to a solid support. The broad concept of this aspect of the invention is illustrated in FIG. 1. In this figure, a heterofunctional linking group is depicted (as 1A) having three functional groups (X, Y and Z) attached via linkers ($L^1$, $L^2$ and $L^3$) to a central core (W). The first functional group is one which provides a non-covalent association with a targeted protein or a protein of interest. For example, the heterofunctional linking group can form a non-covalent association complex (1B) with a protein having a suitable tag (e.g., a his-tag). The second functional group can then establish a covalent linkage to the protein at a site which is proximate to the initial non-covalent association site. One of skill in the art will appreciate that although the protein in 1B is shown as a relatively small circle (relative to the size of the heterofunctional crosslinking group), in fact the protein in most embodiments is quite large relative to the crosslinking group. Nevertheless, the site for covalent attachment of functional group Y will depend on the lengths and flexibility of the linking groups $L^1$ and $L^2$. Typically, the site for covalent attachment of Y to the protein will be between the site of binding of X and about one diameter of the protein, preferably about 50 Å, more preferably about 25 Å, and still more preferably about or less than 10 Å. Release of the non-covalent functional group (X) from the protein provides composition 1C, a protein having a covalently bound heterofunctional crosslinking group. In subsequent steps, functional group Z of the protein-crosslinking group composition can be used, for example, to attach a suitable label to the protein, or to immobilize the protein on a suitable support.

Other aspects of the invention are illustrated in FIGS. 2–4.

In FIG. 2, a recombinant protein is provided having an engineered helical portion capable of forming a "leucine zipper." The recombinant protein is brought into contact with a heterofunctional crosslinking reagent having a helical peptide portion suitable for formation of a leucine zipper, a photoactivateable crosslinking group (Y), and a functional group that is unreactive toward groups normally present in a protein (Z). After formation of the "zippered" non-covalent complex, a photocrosslink is established by illuminating the complex with an appropriate wavelength of light. Typically, the site for covalent attachment of Y to the protein will be within about 50 Å of the site of non-covalent association. In subsequent steps, functional group Z of the protein-crosslinking group composition can be used, for example, to attach a suitable label to the protein, or to immobilize the protein on a suitable support.

A related approach is outlined in FIG. 3. In this figure, a recombinant protein of interest is provided having an introduced helical peptide bearing at least four cysteine residues. The positions of the cysteines are such that a complex can form between pairs of the cysteine residues and an organoarsenical group (preferably one containing at least two arsenic groups) present in a heterofunctional crosslinking reagent. Following formation of the covalent complex, a photocrosslink is established by illuminating the complex with an appropriate wavelength of light. The org,anoarsenical portion can then be removed from the complex to provide the target protein having a covalently bound tether and a new functional group (Z) that is unreactive toward groups typically present in a protein. However, functional group Z can be used, for example, to attach the protein to a surface or to attach a label to the protein.

Yet another related approach is outlined in FIG. 4. In this approach a crosslinker-presenting macromolecule is constructed by attaching the presenting macromolecule (or tag binder) to the crosslinker via a reversible (or cleavable) bond. The crosslinker-presenting macromolecule is contacted with a recombinant protein having an engineered affinity tag to form a non-covalent association complex. A covalent complex is formed by irradiating the non-covalent complex to attach the photocrosslinking group Y to the protein. Subsequent to forming the covalent crosslinking, the bond between the presenting macromolecule and the crosslinker is cleaved (chemically or enzymatically), and the presenting macromolecule is either degraded or released from the peptide tag. The remaining composition (protein having an attached reactive functional group Z) can be modified to attach a label (step 6a) or attached to a solid support (step 6b).

While many of the compounds described herein are set forth as heterofunctional crosslinking reagents, one of skill in the art will understand that additional functional groups can be present on the reagent and can be used to attach other molecules (e.g., for multiple labels) or can be present to provide desired properties (e.g., additional hydroxy substituents on the linking groups can increase the hydrophilicity of the reagent and improve the performance of a protein array by increasing the wettability of the array). Accordingly, in its broadest sense, the present invention provides crosslinking reagents which comprise at least three distinct functional groups (described below as X, Y and Z) linked together in a manner which allows for reaction at each site without interference of the other sites.

In view of the broad utility of the crosslinking groups provided herein, the invention also contemplates compositions of protein-crosslinking groups, methods of introducing labels into a protein at a known location, methods of immobilizing proteins on solid support, single immobilized proteins, arrays of immobilized proteins, and the like.

DESCRIPTION OF THE EMBODIMENTS

In view of the disclosure above, the present application provides a number of crosslinking reagents as well as a variety of methods wherein a protein can be modified with a crosslinking agent to render the modified protein suitable for the attachment of a label or to make the modified protein suitable for attachment to a surface, for example in array preparation.

As will be apparent from the description below, the present invention also provides labeled and/or support-bound proteins that are prepared using the crosslinking reagents described below.

Crosslinking Reagents

Heterofunctional Crosslinking Reagents

In one aspect, the present invention provides a heterofunctional crosslinking reagent having the formula:

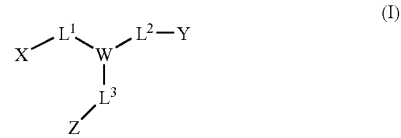

(I)

wherein W is a covalent core component; $L^1$, $L^2$ and $L^3$ are independently linking groups; X is a reversibly covalent or non-covalent protein tag binder; Y is an activatable, preferably a photoactivatable, covalent crosslinking group; and Z is a protected or unprotected covalent crosslinking group.

The covalent core component W can be a variety of structures which provide the appropriate scaffolding for the attachment of linking groups ($L^1$, $L^2$ and $L^3$) and functional groups (X, Y and Z). Typically, the core component and linking groups will provide sufficient distance between the functional groups so that there is little or no steric crowding at the attachment sites (e.g., X, Y and Z). Preferably, the core component is a residue of a moiety having at least three reactive groups which can be carboxyl, amino, hydroxyl, thiol, or the like.

In one group of embodiments, the core component is the residue of an amino acid having a reactive functional group in the side chain (e.g., lysine, serine, aspartic acid, glutamic acid, cysteine and the like). Alternatively, the core component is a modified amino acid (e.g., S-carboxymethyl-L-cysteine, and other suitable derivatives of natural and unnatural amino acids such as homoserine).

Alternatively, the core component can be a substituted hydrocarbon (e.g, a substituted alkyl group or a substituted aryl or heteroaryl group). In this group of embodiments, W can be a tri- or tetra-substituted carbon atom (e.g, the α-carbon of an α-amino acid). For those embodiments in which W is the α-carbon of an α-amino acid, the pendent group-$L^3$-Z can be the functionalized side chain of an amino acid (e.g, a serine sidechain, an aspartic acid side chain, and the like). Alternatively, when W is the α-carbon of an α-amino acid, the pendent group-$L^3$-Z can be the amino group or the carboxylic acid group of the amino acid.

One of skill in the art will appreciate that a variety of other core components can provide the required scaffolding for the linking groups and functional groups including, for example, an amino group, a trivalent boron or boronate ester, or a trivalent or tervalent phosphorus group (e.g., a phosphine, phosphite, phosphate, phosphonate and the like).

In another group of embodiments, the core component can be derived from a glycerol or sugar moiety. A variety of sugars are available having orthogonally protected (and specifically removable) protecting groups which can be used in preparation of the heterofunctional crosslinkers described herein.

Attached to the core component are three linking groups $L^1$, $L^2$ and $L^3$, one or more of which can be optional (e.g., can be a bond), depending on the size of the core component W. Typically, the linking groups $L^1$, $L^2$ and $L^3$ are of sufficient length to permit attachment of a protein to a surface, or attachment of a label to a protein such that the properties of the protein are not compromised by the attached surface or label. For those aspects of the invention below wherein $L^3$ is used to attach to a label, a shorter linking group of, for example, 6 atoms or less is preferred. For those aspects of the invention below wherein $L^3$ is used to attach to a support, a longer linking group of, for example, 10, 20 or 30 atoms or more is preferred. The linking groups, when present, are typically 2–50 atoms long and comprise a core-attaching portion (e.g., a reactive group) and a functional group-attaching portion (e.g, a second reactive group). The central portion of the linking group is typically a longer chain portion and can be a variety of relatively inert organic residues. For example, ethylene glycol monomers or oligomers, diamines, diacids, alkylene groups, heteroalkylene groups, aryl acetylenes and the like. Preferably, the linking group will be a substituted or unsubstituted alkylene group (of from about 2 to about 24 carbons in length), a substituted or unsubstituted heteroalkylene group (of from about 2 to about 24 carbons in length), a polyethyleneglycol group (of from about 2 to about 24 ethyleneglycol monomers in a linear configuration), a polyalcohol group, a polyamine group (e.g., spermine, spermidine and polymeric derivatives thereof), a polyester group (e.g., poly(ethyl acrylate) having of from 3 to 15 ethyl acrylate monomers in a linear configuration), or a polyphosphodiester group. More preferably, the linking group will be a substituted or unsubstituted alkylene group (of from about 6 to about 24 carbons in length), a substituted or unsubstituted heteroalkylene group (of from about 6 to about 24 carbons in length), or a polyethyleneglycol group which is at least a tetraethyleneglycol, and more preferably, from about 1 to 4 hexaethyleneglycols linked in a linear array. For use in synthesis of the heterofunctional crosslinking compounds of the invention, the linking group will typically be provided with functional groups which can be selectively protected or activated.

In one group of embodiments, the linking groups are covalently attached to both the core component and the distal functional group (X, Y or Z) by means of, for example, an ether, thioether, ester, amide, carbamate, sulfate ester, phosphate ester, disulfide, hydrazone or amine linkage. Still further, the linking groups can also be modified or substituted to increase or decrease the hydrophobicity/hydrophilicity of the resultant heterofunctional crosslinking group.

In one group of embodiments, the linking group $L^1$ is a group providing a cleavable attachment to X. A variety of linking groups are known to be cleavable and can be selected to provide a specific type of scission under certain conditions. The use of linking groups containing carboxylic acid esters are sometimes preferred, where this group can be hydrolyzed enzymatically or chemically. Additional linkages can be selected so that it is cleavable by chemical agents or by enzymatic activity (e.g., linkages containing disulfide groups or amide groups).

In some embodiments, $L^1$ is a specifically cleavable linker, having for example, a protease recognition site or other such specifically recognized enzymatic cleavage site and can be used to link X to the crosslinking reagent. A linking group containing phosphate, diphosphate, a dinucleotide, or an oligonucleotide may constitute an enzymatically cleavable linkage, and can be cleaved by various phosphotransferase enzymes, such as phosphatases or ribonucleases that specifically hydrolyze these bonds. Still other types of esters can be used in this manner and cleaved by less specific esterase enzymes. Alternatively, chemical or other types of linkers that are cleavable by, for example, exposure to light or other stimulus can be used to link X to the crosslinking reagent.

Attached to the distal end of each of the linking groups is a functional group or binding group which can be a reversibly covalent or non-covalent binding group (X) or a covalent binding group (Y and Z). More particularly, attached to the distal end of $L^1$ is X, to $L^2$ is Y and to $L^3$ is Z. Each of the functional groups (X, Y and Z) is distinct from the other two. In particular, X is a group which forms a non-covalent association complex with a suitably modified protein or with an available epitope present in the protein, or X can be a component that specifically and reversibly binds to a protein or modified protein in a covalent manner. In one group of preferred embodiments, X is a group which forms a non-covalent association complex with a protein tag (e.g, X is a protein tag binder).

A variety of protein tag binders are useful for forming a non-covalent or reversibly covalent association between the heterofunctional crosslinking reagent and the protein. In one group of embodiments, the protein tag binder is one that binds a protein fusion tag. Accordingly, the protein tag binder will typically be selected to specifically bind a fusion tag and will depend on the selection of such a tag for a particular protein. Selection of an appropriate fusion tag will in turn depend on a number of considerations, including for example, a desired position of non-covalent association (e.g., N-terminus labeling, C-terminus labeling or internal labeling). Examples of suitable fusion tags include T7 tag, S tag, His tag, GST tag, PKA tag, HA tag, c-Myc tag, Trx tag, Hsv tag, CBD tag, Dsb tag, pelB/ompT, KSI, MBP tag, VSV-G tag, β-Gal tag, and GFP tag.

More particularly, the fusion tag/tag binder pairs (wherein X is the tag binder) can be any of the following:

| Fusion tags | Tag binders |
| --- | --- |
| His (6–8 aa) | NTA (Nitrilotriacetic acid, with a metal such as Ni, Co, Fe, Cu) |
| GST (220 aa) | GSH (Glutathione, 3 amino acids) |
| S (104 aa) | S-peptide (15 amino acids) |
| PKA peptide (5 amino acids) | PKA |
| HA peptide (9 amino acids) | HA |
| KSI (125 aa) | OligoPhenylalanine, or OligoLeucine (10–30 amino acids) |
| Arg (6–10 Arg) | OligoGlutamic acid (10–15 amino acids) |
| Asp (6–10 Asp) | OligoArginine (10–15 amino acids) |
| MBP (360 aa) | Maltose |
| GBD | Galactose |
| CBD (107–156 aa) | Cellulose |
| Streptavidin | HPQ peptides (5–12 amino acids) |
| Thioredoxin | Phenylarsine oxide |

From the group of pairs provided above, X can be generally described as a chelating agent (NTA complexes), a peptide (e.g., glutathione) or a carbohydrate (e.g., maltose).

Turning first to those embodiments in which X is a peptide, suitable pairs are GST/glutathione, S tag/S peptide, PKAlArgArgAlaSerVal peptide, HA/HA epitope tag, KSI/oligoPhe or oligoLeu, and the complementary amino acid pairs (including leucine zippers).

The Glutathione S-Transferase (GST) tag is a 220 amino acid protein that binds with high affinity to the tripeptide (γ-Glu-Cys-Gly), glutathione (GSH) and is commonly used as a fusion partner when expressing proteins in *E. coli*. An advantage of this fusion pair is that mild elution conditions can be used, an important factor for many proteins which are sensitive to extreme pH or high salt conditions. Also, quantitation of soluble GST fusions is possible by assaying the transferase activity. See, Smith, et al., *Gene*, 1988, 67, 31–40.

The S fusion tag is a 15 amino acid peptide that binds with high affinity to the 104 amino acid S-protein derived from pancreatic ribonuclease A. The unique property of reconstituting enzymatic activity by the S Tag and S-protein interaction (known as ribonuclease S) enables sensitive quantitative measurement and purification of any fusion protein. The detection can be carried out in a variety of formats, including Western Blot, dot blot, ELISA, and high throughput applications using recombinant proteins. See, Kim, et al., *Protein Sci.*, 1993, 2, 348–356; Richards, et al., in *Enzymes, Vol. IV (Boyer, P. D. Ed.)* 1971, p. 647–806, Academic Press, New York; and Keleman, et al., *Nucleic Acids Res.*, 1999, 27, 771–777.

The PKA/ArgArgAlaSerVal pair is based on the catalytic subunit of cAMP-depedent protein kinase (protein kinase A, PKA), which binds with high affinity with a five amino acid sequence (ArgArgAlaSerVal, known as PKA recognition sequence). It is a powerful system for evaluating protein: protein interactions, especially site-specific labeling of phosphorylation sites. See, Blanar, et al., *Science*, 1992, 256, 1014–1018; and Arthur, et al., *J. Biol. Chem.*, 1998, 273, 31381–31387.

The hemagglutinin (HA) protein has an epitope that binds with high affinity to the nine amino acid peptide (TyrProTyrAspValProAspTyrAla, known as HA epitope tag). This has been demonstrated to be a highly efficient fusion system for the purification of redox enzymes and highly hydrophobic proteins. See, Waterman, et al., *J. Cell. Biol.*, 1997, 139, 1419–1431.

The Ketosteroid Isomerase (KSI) tag is a 125 amino acid protein with highly expressed hydrophobic domain, typically used in the high yield production of peptides and small proteins. The KSI fusion protein is expressed at high levels in the presence of T7 RNA polymerase. KSI has affinity with hydrophobic oligoamino acids, such as oligophenylalanine and oligoleucine, etc. See, Kuliopulos, et al., *J. Am. Chem. Soc.*, 1994, 116, 4599–4607.

Certain oligoamino acid tags are also useful. The affinity is based on the amino acid side chain interaction with complementary charges present at physiological pH, the acidic (negative charged) Asp, Glu and basic (positive charged) Arg. Typically, the complementary binding pairs comprise at least about 6–10 consecutive residues (e.g., Arg Tag having 6–10 consecutive arginine residues which is complementary to an Asp tag binder having 6–10 consecutive aspartic acid residues. see Kohler, et al., *Biotechnol.*, 1991, 9, 642–646. One of skill in the art will appreciate that the tag/tag binders can be reversed. For example, in one embodiment, a fusion protein can be generated having an Arg tag which is complementary to a crosslinking group having an Asp tag binder as X. Alternatively, the protein can be constructed having an Asp tag which is complementary to a crosslinking group having an Arg tag binder.

The protein streptavidin binds with micromolar affinity to various peptides containing the core sequence His-Pro-Gln (see, Katz, Biomolecular Engineering 16:57–65 (1999)), identified using phage display. Such peptides may be from 5 to 12 amino acids in length, and some of these are constrained by di-sulfide bonds between cysteine residues at either side of the His-Pro-Gln sequence.

Thioredoxin is a small single domain protein that is often genetically fused to proteins of interest to increase their expression level and solubility in *E. coli*. Unlike most proteins, thioredoxin has a pair of cysteine residues in close proximity, and the pair of thiols associated with these residues can interact to form a double-covalent bond with a phenylarsine oxide group. One suitable system is described in the Invitrogen catalog (Invitrogen, 1600 Faraday Ave., Carlsbad, Calif., USA: also www.invitrogen.com). Invitrogen has commercialized a system for purifying thioredoxin-fusion proteins using 4-aminophenylarsine oxide-conjugated agarose.

In still other embodiments, the peptide tag/tag binder combinations can be a leucine zipper. In this embodiment, the "zipper" consists of a pair of peptides. Each peptide adopts a helical configuration (typically having from about 20 to 30 amino acids) having leucine side chains. The two helices can then adopt a parallel orientation in which the leucine residues of each helix form a "stacked" configuration between the helices. See, for example, Hurst in *Tran-* scription factors 1. bZIP proteins, Vol. 1(2), 1995, p. 123–168, Academic Press, London and Latchman, in Eukaryotic Transcription Factors, 1991, Academic Press, London.

In another group of embodiments, the protein tag binder is a group which binds an endogenous protein tag (e.g., an epitope on the protein). In this group of embodiments, the protein tag binder will typically be an antibody or antibody fragment which is sufficient to form a non-covalent association complex with the protein tag or epitope.

Turning next to those embodiments in which X is a metal chelating group, the protein tag binder will be in one embodiment a nitriliotriacetic acid group which forms a complex with, for example, nickel ($Ni^{+2}$) and recognizes a His-tag present on a protein. This binding pair is based on the remarkable selectivity of unique Ni-NTA or Co-NTA for proteins having an affinity tag of six to eight consecutive histidine residues, the His tag. This interaction has been used for purification, detection, and assay of essentially any His-tagged protein from an expression system.

Another attractive feature of the His tag is its size which is much smaller than most other affinity tags. Additionally, the His tag is unchanged at physiological pH and rarely alters or contributes to protein immunogenicity. Moreover, the His tag rarely interferes with protein structure or function, does not require removal by protease cleavage, and is compatible with a variety of denaturing buffer systems. See Sisk, et al., *J. Viol,* 1994, 68, 766; Hochuli, et al., *Biotechnol.* 1988, 1321–1325; and Hochuli, et al., *J. Chromatogr.,* 1987, 411, 177–184. Alternatively, NTA complexes of $Ni^{+2}$ have also been shown to bind zinc-finger proteins (see Kadouri, et al., *J. Virol. Methods,* 1998, 76, 19–29). NTA complexes of $Fe^{+3}$ have been shown to bind phosphoproteins (see Andersson, et al., *Anal. Chem.* 1986, 154, 250–254; and Muszynska, et al., *Biochem.,* 1986, 25, 6850–6853).

In still another group of embodiments, X can be a carbohydrate group which is recognized by certain proteins or protein tags (e.g, Maltose binding proteins or MBP tags, Galactose binding proteins or GBP tags, and Cellulose binding proteins or CBD tags). Fusion of a target protein to a carbohydrate-binding protein is particularly attractive as the tag binder is cost effective and is susceptible to treatment with heat or alkali. In addition, the low cost of the tag binder makes it feasible to perform competitive elution with ligand-containing buffers. These are especially suited for protein immobolization and bioaffinity separation.

In other embodiments, X can be a small molecule (e.g., a ligand, natural product or inhibitor) with particular affinity for a protein ($K_d$ of less than about $10^{-6}$ M). Preferably, the small molecule will have a molecular weight of 2000 Daltons or less. For example, X can be FK 506 which binds an FK binding protein (see Hung, et al., *Chem. Biol.* 1996, 3, 623–639); Cyclosporin which binds a Cyclophilin or Cyclosporin-binding protein; or another ligand, inhibitor or binding peptide (see Hinterding, et al., *Angew. Chem. Int. Ed.,* 1998, 37, 688–749; Babine, et al., *Chem. Rev.* 1997, 97, 1359–1472; MacKintosh, et al., *Trends Biochem. Sci.* 1994, 19, 444–448; and Van der Geer, et al., *Annu. Rev. Cell Biol.,* 1994, 10, 251–337).

The present invention further contemplates those embodiments in which X is a small oligonucleotide having specificity for a DNA-binding protein (e.g., a bZIP transcription factor). See, Dennison, et al., *Chem. Biol.,* 1998, 5, 1–17; Kodadek, *Chem. Biol.,* 1995, 2, 267–279; and Hurst, in *Transcription factors* 1: *bZjPproteins,* Vol. 2 (2), 1995, p. 105–168, Academic Press; London. Still other non-covalent binding pairs are known to those of skill in the art and provide one member (X) which is useful in the present crosslinking reagents and in other aspects of the invention discussed below.

In still other embodiments, X is an organoarsenical group, typically one having at least one arsenic atom, and preferably one having two or more arsenic atoms. A variety of organoarsenical groups are useful in this aspect of the invention. Preferably, organoarsenical group comprises an organic ring scaffold (e.g., an aromatic ring or rings) having attached arsenic atoms that are positioned and available for binding to cysteine residues in a peptide or protein helical coil. In one embodiment, the organoarsenical group is an anthracene group, or a heterocyclic version thereof, having attached arsenic atoms at the 1- and 8-positions of the tricyclic ring system. Alternatively, the organoarsenic group can be a biphenyl moiety wherein each phenyl ring bears an arsenic atom. See Griffin et al., *Methods in Enzymology,* vol. 327, pages 565–578 (2000).

Functional group Y is a photoactivatable covalent linking group. A variety of photoactivatable groups can be used and are selected to be responsive to a particular portion of the electromagnetic spectrum. Preferred groups are those which are reactive in response to ultraviolet or visible portions of the light spectrum. Still more preferably, the photoreactive groups are those which will generate an active species (photoactivatable) when exposed to an external light source. The active species will then react with an adjacent chemical group to form a new covalent bond. Generally, the active species will be a free radical group such as a nitrene, carbene or an excited state of a ketone. Examples of groups capable of forming free radicals in response to ultraviolet or visible light include, for example, aryl ketones, azides, diazo compounds, diazirenes, and ketenes. See, Pierce Products Catalog, 1999–2000, pages 147–276, and Hermanson, BIOCONJUGATE TECHNIQUES, Academic Press, San Diego Calif., 1996.

Photoactivatable aryl ketones include benzophenones, acetophenones, anthraquinones, anthrones, and related heterocyclic derivatives (those having an oxygen, nitrogen or sulfur atom replacing a carbon in the ring system). In addition, substituted versions of each of the above-noted aryl ketones are also contemplated by the present invention.

Another class of photoactivatable groups are the azides, including the aryl azides (e.g., phenyl azide and substituted phenyl azides), acyl azides (e.g., benzoyl azide), azido formates (e.g, ethyl azidoformate, phenyl azidoformate), sulfonyl azides (e.g., benzenesulfonyl azide) and the phosphoryl azides (e.g., diphenyl phosphoryl azide and diethyl phosphoryl azide).

Still another class of photoactivatable groups are the diazo compounds, such as the diazoalkanes (e.g., diazomethane and diphenyldiazomethane), diazo ketones (e.g., diazoacetophenone and 1-trifluoromethyl-1-diazo-2-pentanone), and diazoacetates (e.g., t-butyl diazoacetate and phenyl diazoacetate).

Still other photoactivatable groups are the diazirenes (e.g., 3-trifluoromethyl-3-phenyldiazirene) and the ketenes (e.g., ketene and diphenyl ketene). Additional photoactivatable groups are known to those of skill in the art and can be used in the present invention. See, for example, Bayley, PHOTOGENERATED REAGENTS IN BIOCHEMISTRY AND MOLECULAR BIOLOGY, eds. T. Work and R. Burdon, Elsevier, Amsterdam (1983) and Kuechler, et al., PHOTOCHEMICAL PROBES IN BIOCHEMISTRY, ESCOM Science, Dordrecht, The Netherlands (1989).

As used herein, the term "photoactivatable" is also meant to include any reactive functional group that is protected by a photoremovable or photolabile protecting group. Suitable photolabile protecting groups can be found in, for example, Greene, et al., PROTECTIVE GROUPS IN ORGANIC CHEMISTRY, 2nd Ed., John Wiley & Sons, New York, N.Y, 1991.

Functional group Z is a reactive group which can form a covalent link to another molecule, label or support, and which is optionally protected. Preferably, Z is a group which can participate in a chemoselective ligation reaction having little or no cross reactivity with functional groups present in the amino acids that make up the protein being modified. Alternatively, the reactive Z groups can exert some cross reactivity if the groups are activated in proximity to the desired target under conditions wherein bond formation with the target is favored over reactivity with other sites. Examples of such reactive groups (or covalent linking groups) include acyl hydrazines (which can react with a ketone on a surface for form an acyl hydrazone), olefins (which can react with a second olefin on a surface or as part of a label in a cross olefin metathesis catalyzed by, for example, a ruthenium complex), or a diketone (which can react with a guanidine group). Other covalent linking groups useful in the present invention include epoxides, aldehydes, reactive esters (e.g., pentafluorophenyl esters, nitrophenyl esters), isocyanates and thioisocyanates, carboxylic acid chlorides, disulfides and sulfonate esters (e.g, mesylates, tosylates and the like). Still other covalent linking groups are the sulfhydryl groups (preferably protected until reaction is desired). Other suitable covalent linking groups include, but are not limited to, maleimide, isomaleimide, N-hydroxysuccinimide (Wagner et al, *Biophysical Journal*, 1996, 70:2052–2066), nitrilotriacetic acid (U.S. Pat. No. 5,620,850), activated hydroxyl, haloacetyl, activated carboxyl, hydrazide, epoxy, aziridine, sulfonylchloride, trifluoromethyldiaziridine, pyridyldisulfide, N-acyl-imidazole, imidazolecarbamnate, vinylsulfone, succinimidylcarbonate, arylazide, anhydride, diazoacetate, benzophenone, isothiocyanate, isocyanate, imidoester, fluorobenzene, and the like.

As noted above, Z will in some embodiments be protected, or otherwise rendered inactive to covalent bond formation, by a protecting group. A variety of protecting groups are useful in the invention and can be selected based on the functionality present in Z. The term "protecting group" as used herein, refers to any of the groups which are designed to block one reactive site in a molecule while a chemical reaction is carried out at another reactive site. More particularly, the protecting groups used herein can be any of those groups described in Greene, et al., Protective Groups In Organic Chemistry, 2nd Ed., John Wiley & Sons, New York, N.Y, 1991. The proper selection of protecting groups for a particular synthesis will be governed by the overall methods employed in the synthesis. For example, in automated synthesis photolabile protecting groups such as NVOC, MeNPOC, and the like can be used. However, the use of suitable photolabile protecting groups will typically involve consideration of such parameters as the wavelength at which the groups can be removed in order to render the groups selectively removable when in the presence of the photoactivatable groups (Y). In other embodiments, protecting groups may used that are removeable by chemical methods, such as FMOC, DMT and other methods known to those of skill in the art.

Leucine-Zipper Crosslinking Reagents

In another aspect, the present invention provides a crosslinking reagent having the formula:

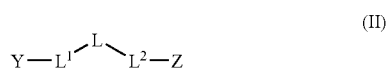

wherein L is a helical component of a leucine zipper; $L^1$ and $L^2$ are each independently selected from the group consisting of a bond and a linking group; Y is a photoactivatable crosslinking group; and Z is a protected or unprotected chemical crosslinking group.

In this aspect of the invention, the crosslinking compound or reagent is based on a nucleus L, that is a helical component of a leucine zipper. The use of leucine zippers is described in, for example, Hurst in *Transcription factors* 1: *bZIP proteins*, Vol. 1(2), 1995, p. 123–168, Academic Press, London and Latchman, in *Eukaryotic Transcription Factors*, 1991, Academic Press, London.

A helical coiled coil is a structural protein or peptide motif in which a pair of α-helices coil around each other, similar to the twin strands of the DNA double-helix. The peptide α-helices have about 3.6 residues per turn, which means that about every seventh residue occupies a roughly equivalent position with respect to the helix axis. The simplest and most well-studied types of coiled coils are the "leucine zippers", characterized by the presence of leucine residues at about every seventh position of each α-helix. This regular array of leucines creates a hydrophobic—literally "water fearing"—surface that runs along one side or face of each α-helix. Such surfaces attract each other by shielding themselves from the surrounding water, as well as through van der Waals interactions, thus causing dimerization of two such α-helices.

The length and sequence of leucine zippers determines whether they form homo- or hetero-dimers, whether they are parallel or antiparallel, and the strength of their interaction. The types of zippers most useful for the purposes described herein are those that form exclusively heterodimers with a unique orientation (parallel or antiparallel). These parameters can be controlled by the choice of the peptide sequence including, but not limited to, the use of positively and negatively charged residues at the ends of the helices that would strongly favor a single dimerization state. Additionally, the length of the helices can be tailored to provide sufficient length for a strong interaction (e.g. $K_d$<100 nM), yet short enough to allow high solubility in aqueous conditions. In preferred embodiments, the L component has from about 12 to about 50 amino acid residues and about two to about six leucine residues spaced at every seventh position on the helical coil. More preferably, the L component has from about 24 to about 42 amino acid residues and about three to about five leucine residues spaced at every seventh position on the helical coil.

Attached to L are two linking groups $L^1$ and $L^2$, one or both of which can be optional (e.g., can be a bond), depending on the point of attachment to L. Typically, the linking groups $L^1$ and $L^2$ are of sufficient length to permit flexibility in the attachment of a protein to a surface, or attachment of a label to a protein such that the properties of the protein are not compromised by the attached surface or label. For those aspects of the invention below wherein $L^2$ is used to attach to a label, a shorter linking group of, for example, 6 atoms or less is preferred. For those aspects of the invention below wherein $L^2$ is used to attach to a support, a longer linking group of, for example, 10, 20 or 30 atoms or more is preferred. The linking groups, when present, are typically 2–50 atoms long and can be a variety of relatively inert organic residues. For example, ethylene glycol monomers or oligomers, diamines, diacids, alkylene groups, heteroalkylene groups, aryl acetylenes and the like are suitable. Preferably, the linking group will be a substituted or unsubstituted alkylene group (of from about 2 to about 24 carbons in length), a substituted or unsubstituted heteroalkylene group (of from about 2 to about 24 carbons in length), a polyethyleneglycol group (of from about 2 to about 24 ethyleneglycol monomers in a linear configuration), a polyalcohol group, a polyamine group (e.g., spermine, spermidine and polymeric derivatives thereof), a polyester group (e.g., poly(ethyl acrylate) having of from 3 to 15 ethyl acrylate monomers in a linear configuration), or a polyphosphodiester group. More preferably, the linking group will be a substituted or unsubstituted alkylene group (of from about 6 to about 24 carbons in length), a substituted or unsubstituted heteroalkylene group (of from about 6 to about 24 carbons in length), or a polyethyleneglycol group which is at least a tetraethyleneglycol, and more preferably, from about 1 to 4 hexaethyleneglycols linked in a linear array. For use in synthesis of the crosslinking compounds of the invention, the linking groups will typically be provided with functional groups that can be selectively protected or activated.

In one group of embodiments, the linking groups are covalently attached to both the helical component and the distal finctional group (Y or Z) by means of, for example, an ether, thioether, ester, amide, carbamate, sulfate ester, phosphate ester, dissulfide, hydrazone or amine linkage. Still further, the linking groups can also be modified or substituted to increase or decrease the hydrophobicity/hydrophilicity of the resultant heterofunctional crosslinking group.

Attached to the distal end of each of the linking groups is a functional group or binding group which is typically a covalent binding group (Y and Z). More particularly, attached to the distal end of $L^2$ is Y, and to $L^2$ is Z.

Functional group Y is a photocrosslinking group. A variety of photoactivatable groups can be used and are selected to be responsive to a particular portion of the electromagnetic spectrum. In general, the Y groups in this aspect of the invention are the same as those described above for compounds of formula (I). Similarly, preferred Y groups are those described above as preferred.

Functional group Z is a reactive group that can form a covalent link to another molecule, label or support, either directly or indirectly via a homo- or heterobifunctional crosslinking group. Additionally, Z can be optionally protected. Generally, Z can be any of those groups described above for Z in formula (I).

Protein Labeling Reagents

In another aspect, the present invention provides protein labeling reagents having the formula:

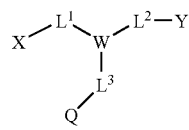

(III)

wherein W is a covalent core component; $L^1$, $L^2$ and $L^3$ are each independently linking groups; X is a reversibly covalent or non-covalent protein tag binder; Y is a photoactivatable covalent crosslinking group; and Q is a label or a reporter group. The symbols W, X, Y, $L^1$, $L^2$ and $L^3$ have been described above with reference to formula (I) and are intended to have the same meaning in this aspect of the invention.

The symbol Q represents a label or reporter group. A variety of labels or reporter groups are useful in this aspect of the invention and are known to those of skill in the art. Preferably, the label is an optically detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives and Oregon Green™, rhodamine and derivatives (e.g., Texas red, etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label is typically coupled directly to the linking group $L^3$ according to methods well known in the art (e.g, via ether, ester, amide, dissulfide, thioether, hydrazone, or acyl hydrazide linkages, and the like). As indicated above, a wide variety of labels may be used, with the choice of label depending on sensitivity required, ease of conjugation with the linking group, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/ Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

In a related aspect, the invention further provides protein labeling reagents having the formula:

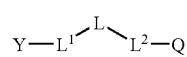

(IV)

wherein L is a helical component of a leucine zipper; $L^1$ and $L^2$ are each independently a bond or a linking group; Y is a photoactivatable covalent crosslinking group; and Q is a label or a reporter group. In this aspect, the components L, $L^1$, $L^2$, and Y can be essentially any of the components described for formula (II) above. Preferred embodiments for L, $L^1$, $L^2$, and Y are also those described for formula (II). The letter Q can be any of those labels or reporter groups provided above with reference to formula (III). Similarly, preferred Q groups are also those described as preferred with reference to formula (III).

Protein Conjugates

In yet another aspect, the present invention provides a protein conjugate having the formula:

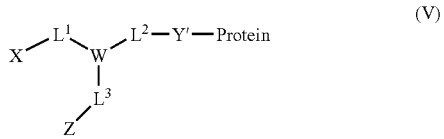
(V)

wherein W is a covalent core component; $L^1$ is a linking group (or the vestige of a linking group following removal of, for example, an organoarsenic component as described above); $L^2$ and $L^3$ are each independently a bond or a linking group; X is H or a covalent or a non-covalent protein tag binder; Y' is a photoactivatable crosslinking group that has been activated and covalently attached to a protein; and Z is a protected or unprotected covalent crosslinking group.

Conjugates of the formula above have particularly attractive utility as commercial reagents which can be attached to essentially any support or labeling group. Still further, the site of covalent attachment can be selected to be removed from active sites, ligand binding sites or drug binding sites of the protein by an appropriate selection of linking group lengths and by site-selective attachment of a protein tag to the protein of interest. For example, a His-tag can be site selectively introduced into a protein using fusion methods described above. A first association complex between a heterofunctional linking group of formula I above and the His-tag modified protein can then be formed by contacting the modified protein with the heterofunctional crosslinking groups under conditions suitable for an association to form. Following formation of the association complex, the photoactivatable group, Y, can be activated to form a covalent bond to the protein at a site proximate to the tag binder/tag association site. Typically, the site of covalent attachment will be within one diameter of the target protein, preferably about 50 angstroms, more preferably 25 angstroms, and most preferable about 10 angtroms of the tag binder/tag site. In preferred embodiments, the site of covalent attachment will be within about 15 angstroms of the tag binder/tag site, more preferably within about 8–10 angstroms of the tag binder/tag site, and most preferably within about 5 angstroms of the tag binder/tag site.

The resultant complex can optionally be subjected to suitable mild conditions to dissociate the non-covalent association between the protein tag or epitope and the tag binder to provide the subject conjugates.

In yet another aspect, the present invention provides a protein composition having the formula:

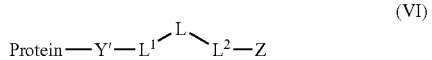
(VI)

In this formula, L is a helical component of a leucine zipper; $L^1$ and $L^2$ are each independently a bond or a linking group; Y' is a photoactivatable crosslinking group that has been activated and covalently attached to a protein; and Z is a protected or unprotected chemical crosslinking group. Preferred groups for L, $L^1$, $L^2$, Y, and Z are the same as those described above with reference to formula (II). Suitable proteins include essentially any full length protein, protein fragment or polypeptide for which labeling information or support-bound assays or diagnostics are desired.

Protein Compositions

In yet another aspect, the present invention provides protein compositions comprising a protein and a crosslinking reagent that is attached to either a label or a solid support. In one group of embodiments, the conjugates have the formula:

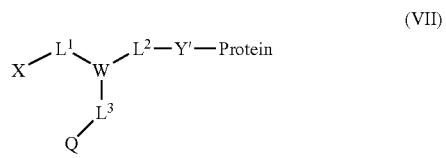
(VII)

wherein, the symbols W, X, $L^1$, $L^2$ and $L^3$ have the meanings and preferred embodiments as described above for formulae (I) and (III), and Y' now represents the residue of a photoactivatable covalent crosslinking group (Y in the compounds of formula I) after formation of a covalent linkage to the protein, and Q is a label or a solid support.

In a related aspect, the present invention provides a protein composition having the formula:

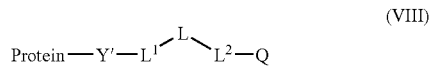
(VIII)

wherein L is a helical component of a leucine zipper; $L^1$ and $L^2$ are each independently selected from a bond and a linking group; Y' is a photoactivatable crosslinking group that has been activated and covalently attached to a protein; and Q is a solid support or a label.

Support-Bound Crosslinking Groups

In yet another aspect, the present invention provides a support-bound crosslinking reagent, having the formula:

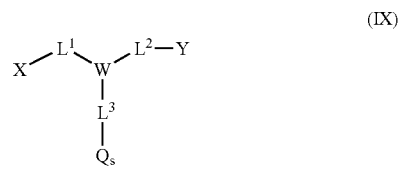
(IX)

In this formula W is a covalent core component; $L^1$ is a cleavable or non-cleavable linking group; $L^2$ and $L^3$ are each independently a bond or a linking group; X is a reversibly covalent or non-covalent protein tag binder; Y is a photoactivatable covalent crosslinking group; and $Q_s$ is a solid support, a monolayer attached to a support, or a thinfllm attached to a support.

In this aspect, the preferred components for W, $L^1$, $L^2$, $L^3$, Y and Z are as described above for formula II. Preferred labels and supports are described below with reference to protein arrays and their uses. For those embodiments in which Q is a solid support, one of skill in the art will appreciate that Q can also be a monolayer attached to a support or a thinfilm attached to a support. A variety of substrates or supports are useful in this aspect of the invention and are described below with reference to protein arrays. Additionally, this aspect of the invention is meant to include those supports having a plurality of attached crosslinking groups (either directly attached to the support, or attached to a monolayer or thinfilm which is attached to a support).

In a related aspect, the invention further provides a support-bound crosslinking composition having the formula:

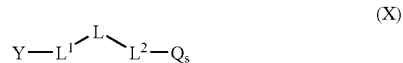 (X)

wherein L is a helical component of a leucine zipper; $L^1$ and $L^2$ are each independently a bond or a linking group; Y is a photoactivatable crosslinking group; and $Q_s$ is a member selected from a solid support, a monolayer attached to a support and a thinfilm attached to a support.

Methods of Attaching Proteins to a Solid Support

In another aspect, the present invention provides a method of attaching a protein to a solid support, the method comprising:

(i) forming a non-covalent association between a protein and a protein tag binder of a heterofunctional crosslinking reagent;

(ii) forming a covalent linkage between the solid support and a first functional group of the heterofunctional crosslinking reagent; and (iii) forming a covalent linkage between the protein and a second functional group of the heterofunctional crosslinking reagent.

Proteins which can be attached to a solid support using the present methods are those which have an accessable epitope that can bind a protein tag binder or those which have been modified to incorporate a suitable tag for binding to a protein tag binder. Preferably, the tag is a peptide or polypeptide having a known binding partner.

A suitable tag is preferably attached to the protein by covalent bonding. For example, one method of obtaining a protein having a peptide or polypeptide tag is to use a heterobifunctional linker to link the protein to the tag. Suitable linkers are known to those of skill in the art. One example of a suitable linker is the heterobifunctional linker SMCC (succinimidyl 4-[N-maleimidomethyl] cyclohexane-1-carboxylate; Sigma Chemical Co., St. Louis, Mo.), which can form a link between an amino residue (for example, lysine) and a thiol (such as that provided by cysteine). Other cross-linkers include, for example, m-maleimidobenzyl-N-hydroxysuccinimide ester (MBS) (Liu et al. (1979) *Biochemistry* 18: 690; Green et al. (1982) *Cell* 28: 477), glutaraldehyde, a carbodiimide succinyl anhydride, N-succinimidyl-3-[2-pyridyldithio]-propionate, and the like.

An additional method by which one can obtain a protein having a suitable tag (e.g., a peptide tag) is to construct a fusion gene in which a nucleic acid that codes for the protein is operably linked to a nucleic acid that codes for the tag. The nucleic acid encoding the tag is preferably placed at a location in the protein gene that does not disrupt the ability of the fusion protein obtained to bind to, for example, its ligand (for a receptor or enzyme). Where the protein of interest is an antibody, the tag-encoding nucleic acid can be placed at or near the region of the antibody gene that encodes the carboxyl terminus of either the light chain or the heavy chain, or both. Methods for constructing and expressing genes that encode fusion proteins are well known to those of skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

One example of a suitable tag, described above, is a polyhistidine sequence, which is capable of binding to metal chelate affinity ligands. Generally, at least two histidine residues are required to obtain binding to the ligand; the use of additional adjacent histidines increases the binding affinity. Typically, six adjacent histidines are used, although one can use more or less than six. Suitable metal chelate affinity ligands that can serve as the protein tag binder for a polyhistidine tag include nitrilo-triacetic acid (NTA) (Hochuli, E. (1990) "Purification of recombinant proteins with metal chelating adsorbents" *In Genetic Engineering: Principles and Methods*, J. K. Setlow, Ed., Plenum Press, NY; commercially available from Qiagen (Santa Clarita, Calif.)). Dissociation of polyhistidine sequences from metal chelate affinity ligands can be achieved by bringing the solution containing the complex to a mildly acidic pH such as, for example, pH 4. Also, one can dissociate the binding between the polyhistidine sequence and the metal chelate affinity ligand (or tag binder, X) by adding to the solution a chelating agent that competes with the His-tag for binding to the tag binder. Suitable chelating agents include imidazole. Other suitable metal chelate affinity ligands and corresponding methods for dissociation are known to those of skill in the art.

Another example of a suitable tag/tag binder pair is the FLAG™ system (Kodak). The FLAG™ molecular tag consists of an eight amino acid FLAG peptide marker that is linked to the target protein. Conveniently, a tag-modified protein having a FLAG™ tag is synthesized by cloning a 24 base pair FLAG coding sequence adjacent to a nucleotide sequence that codes for the protein and expressing the fusion gene in an appropriate expression vector. The FLAG peptide marker also includes an enterokinase recognition site that corresponds to the carboxy-terminal five amino acids. Tag binders suitable for use with the FLAG peptide marker include antibodies that bind to the FLAG™ peptide. For example, the Anti-FLAG M1, M2 and M5 monoclonal antibodies are commercially available. All eight amino acids of the FLAG peptide marker are required for binding of some anti-FLAG monoclonal antibodies; other antibodies may require fewer amino acids. These anti-FLAG monoclonal antibodies differ in their preference for the location of the FLAG marker peptide relative to the protein it is fused to and in their ability to be bound to or released from the FLAG marker peptide in the presence or absence of calcium. The anti-FLAG M1 (IgG2b) monoclonal antibody-binds to the FLAG epitope in the presence of calcium and requires a free amino group on the N-terminal aspartate for high affinity binding. Only the first four amino acids of the FLAG sequence (N-AspTyrLysAsp-C) are required for anti-FLAG M1 antibody binding; the presence of a glutamate at the fifth position (AspTyrLysAspGlu) increases the sensitivity by six-fold (Knappik and Pluckthun (1994) *Biotechniques* 17: 754–761). The anti-FLAG M1 monoclonal antibody is therefore useful as a protein tag binder for binding FLAG peptides that are present on the amino terminus of the target binding moiety. One advantage of the anti-FLAG M1 monoclonal antibody as a protein tag binder is that because its binding to a FLAG epitope is calcium-dependent, one can remove the protein tag binder from the target protein under extremely mild conditions such as by the addition of a chelating agent such as EDTA. Alternatively, dissociation can be accomplished by competition with FLAG peptide. The anti-FLAG M5 (IgG1) monoclonal antibody has a high relative affinity for N-terminal Met-FLAG fusion proteins. N-terminal Met-FLAG fusion proteins are created by placing an ATG translational start codon immediately before the FLAG coding sequence. When transfected into an appropriate host, the N-terminal Met-FLAG fusion protein will be expressed in the cytoplasm of the cell. Unlike the anti-FLAG M1 monoclonal antibody, the binding of the anti-FLAG M5 antibody to the FLAG marker peptide is not calcium dependent. Where the target protein is an antibody that includes a FLAG tag, a preferred tag binder is the anti-FLAG M2 (IgG1) monoclonal antibody, which is also commercially available. This monoclonal antibody binds to the FLAG epitope regardless of its position relative to the remainder of the target binding moiety. Therefore, the FLAG tag can be placed in or near the carboxy terminus of the target binding antibody, thus avoiding disruption of the target analyte binding region. The binding of the anti-FLAG M2 monoclonal antibody is not calcium-dependent, but mild elution of FLAG fusion proteins from anti-FLAG M2 affinity columns can be accomplished by competition with FLAG peptide.

According to the methods described herein, a non-covalent association is formed between a protein (or suitably modified protein) and a protein tag binder of a heterofunctional crosslinking reagent. Typically, the non-covalent association is formed by bringing the two components together is a neutral or buffered medium. The tag binder present in a heterofanctional crosslinking reagent can be any of the groups described above with reference to the reagents of the present invention, or can be any tag binder of a known binding pair. Preferably, the protein tag binder is one that binds a protein fusion tag selected from a T7 tag, S tag, His tag, GST tag, PKA tag, HA tag, c-Myc tag, Trx tag, Hsv tag, CBD tag, Dsb tag, pelB/ompT, KSI, MBP tag, VSV-G tag, β-Gal tag, and GFP tag.

In another group of embodiments, the protein tag binder is a group which binds an endogenous protein tag (e.g., an epitope on the protein). In this group of embodiments, the protein tag binder will typically be an antibody or antibody fragment which is sufficient to form a non-covalent association complex with the protein tag or epitope.

In the most preferred embodiments, the protein tag binder is a nitriliotriacetic acid group which forms a complex with nickel ($Ni^{+2}$) and forms a non-covalent association complex with a His-tag present on a protein.

Following formation of the non-covalent association complex between a protein of interest and the protein tag binder, a covalent linkage can be formed between a solid support and a functional group (depicted and described above as Z) present on the heterofunctional crosslinking reagent. Conditions for the formation of a covalent linkage will depend on the reactive sites present on the solid support as well as the functional group Z and other functional groups present on the protein. Preferably, mild conditions are used (e.g, an aqueous buffered solvent system at ambient temperature).

Alternatively, the protein-heterofunctional linking group conjugate can be irradiated to activate the photoactivatable group, Y, and form a covalent linkage between the photoactivatable group and the protein. Conditions for photoactivation will depend on the group Y. Typically, photoactivation can be accomplished using light, preferably having wavelength within the ultraviolet range (UV), more preferably within the UVB range, still more preferably within about 300–380 nm, more preferably about 315–380 nm and most preferably about 350–380 nm.

In the latter case, once a covalent attachment of the protein to the heterofunctional linking group has been accomplished, the resultant conjugate can be chemically tethered to a solid support as noted above. For example, in some embodiments the Z group will be a protected form of a reactive fimctional group which can be covalently attached to surface Si—OH groups present on a glass substrate. Alternatively, the Z group can be reactive with surface functionalities present in the thinfilms or monolayers described below. Still other methods for attaching the linking group-bound protein to a support can be employed and are readily apparent to those of skill in the art.

Methods for Attaching Crosslinking Reagents to Proteins

The present invention further provides a method for covalently attaching a heterofinctional crosslinking reagent to a recombinant protein having an engineered helical portion, the method comprising:

(i) forming a non-covalent association complex between the engineered helical portion of the recombinant protein and a heteroflnctional crosslinking reagent comprising a peptide helical portion, a photocrosslinking portion and a chemical crosslinking portion that is unreactive to functional groups normally present on a protein; and (ii) illuminating the non-covalent association complex to form a covalent linkage between the recombinant protein and the photocrosslinking group of the heterofunctional crosslinking reagent.

In some embodiments, photocrosslinking may be replaced with non-photon crosslinking or activatable crosslinking.

Preferably, the recombinant protein having an engineered helical portion is a fusion protein that has been engineered to incorporate a first component of a leucine zipper at a site that will not significantly affect the function or binding characteristics of the protein. More preferably, the first component of the leucine zipper is a helical peptide having from about 12 to 50 amino acid residues with at least two leucine residues. Still more preferably, the first component of the leucine zipper is a helical peptide having from about 24 to 42 amino acid residues with at least four leucine residues spaced to project their sidechains from the same side of the helix.

In this aspect of the invention, the heterofunctional crosslinking group is typically a crosslinking group of formula I above, wherein L is the helical portion, Y is the photocrosslinking portion and Z is the chemical crosslinking portion that is unreactive to functional groups normally present on a protein.

Thus, the helix corresponding to one half of the heterodimeric leucine zipper is genetically fused to the protein of interest; while the second half of the heterodimeric leucine zipper is prepared by standard peptide chemistry (see FIG. 2). The latter helix also carries a photocrosslinking portion (e.g., a benzophenone moiety) and a protected or unprotected reactive covalent crosslinking group (non-reactive with proteins) that is suitable for surface immobilization or introduction of a label. The interaction between the two helices in the coiled coil can be stabilized by introducing cysteines into both helices in an arrangement that allows for the formation of a covalent disulfide bridge. Upon illumination at the maximum absorbance of the benzophenone, the chemically synthesized helix would form a covalent bond to the fusion protein. The modified protein could then either be bound to a surface or modified with a label by using the reactive covalent crosslinking group (Z).

Formation of a non-covalent association complex between the engineered protein and the crosslinking reagent (step (i)) can typically be accomplished by bringing the protein and reagent together in an aqueous or substantially aqueous solvent system, that is either neutral or buffered. Additionally, complex formation can be carried out at temperatures of from about −15° C. to about 60° C., preferably from about 4° C. to about 37° C. Organic solvents such as DMSO, DMF, NMP or the like, or detergents can be used to increase the solubility of the leucine zipper peptides.

Following formation of the non-covalent association complex, the complex is illuminated with light of a suitable wavelength to activate the photocrosslinking group and form a covalent linkage between the photoactivatable group (Y, when a reagent of formula II is used) and the protein. Conditions for photoactivation will depend on the group Y. Typically, photoactivation can be accomplished using light having wavelengths of about 300–380 nm, more preferably about 315–380 nm and most preferably about 350–380 nm, as disclosed above.

Photolinking may be substituted with non-photon activated crosslinking, or photon-activated activators in the solution. Accordingly, photoactivation or photocrosslinking may, in some embodiments, be replaced by activation.

Subsequent to forming the covalent crosslinking, the bond between the presenting macromolecule and the crosslinker is cleaved, and the presenting macromolecule is either degraded or released from the peptide tag.

The above steps provide for the attachment of a heterofunctional crosslinking reagent to an engineered protein. The resulting modified protein can then be attached to a variety of other components such as a solid support, a probe or a label, through the remaining reactive functional group present on the heterofunctional crosslinking reagent. For example, in some embodiments the chemical crosslinking portion is a protected form of a reactive functional group that can be covalently attached to surface Si—OH groups present on a glass substrate. Alternatively, the chemical crosslinking portion (Z when reagents of formula I are used) can be reactive with surface flmctionalities present in the thinfilms or monolayers described below. Still other methods for attaching the crosslinking group-bound protein to a support can be employed and are readily apparent to those of skill in the art.

In other embodiments a label or reporter group can be attached to the modified protein through the chemical crosslinking portion of the crosslinking reagent. A variety of labels or reporter groups are useful in this aspect of the invention and are known to those of skill in the art. Preferably, the label is a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry,* 2nd ed., Springer Verlag, N.Y. and in Haugland (1996) *Handbook of Fluorescent Probes and Research Chemicals,* a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives) and Oregon Green™, rhodamine and derivatives (e.g., Texas red, etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label is typically coupled directly to the linking group $L^3$ according to methods well known in the art (e.g, via ether, ester, amide, dissulfide, thioether, hydrazone, or acyl hydrazide linkages, and the like). As indicated above, a wide variety of labels may be used, with the choice of label depending on sensitivity required, ease of conjugation with the linking group, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/ Gibco BRL; 2) color production (using both horseradish peroxidase and/or alkaline phosphatase with substrates that produce a colored precipitate, preferably at the site of activity, [kits available from Life Technologies/ Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags; 5) radioactivity. Other methods for labeling and detection will be readily apparent to one skilled in the art.

In yet another aspect, the present invention provides a method for attaching a crosslinking reagent to a recombinant protein having an engineered peptide portion comprising at least four cysteine residues, said method comprising:

(i) forming a covalent complex between the engineered peptide portion of the recombinant protein and a heterofunctional crosslinking reagent, wherein the heterofanctional crosslinking reagent comprises an organoarsenical group reactive with the at least four cysteine residues present in the engineered helical peptide portion, a photocrosslinking portion and a chemical crosslinking portion that is unreactive to functional groups normally present on a protein;

(ii) illuminating the covalent complex to form a covalent linkage between the recombinant protein and the photocrosslinking group of the heterofrnctional crosslinking reagent; and (iii) releasing the organoarsenical group from the protein and the crosslinking reagent to provide a recombinant protein having an attached crosslinking reagent.

Photocrosslinking, may replace non-photon mediated crosslinking.

There are few known examples of compounds that form covalent bonds with certain peptide sequences but are otherwise unreactive towards proteins. One system for accomplishing this takes advantage of the covalent interaction between pairs of thiols and trivalent organoarsenicals. A compound called FLASH has been synthesized that is based on fluorescein, but possesses two arsenic atoms (Griffin et al, *Science* 1998, 281, 269–272). An artificial helical peptide has been designed that contains four cysteine residues spaced in such a way that they can simultaneously engage the two arsenic groups on FLASH. The interaction is highly specific for this helical sequence when low concentrations of competing vicinal dithiols such as 1,2-ethanedithiol are present in the solution.

Accordingly, in this aspect of the invention, an engineered protein is provided having a helical peptide with suitably placed cysteine residues for engaging the two arsenic groups on FLASH. Such a protein is similar to the proteins described above having a leucine zipper component with the exception that the helical portion is designed to provide cysteine residues rather than leucine residues projecting from the face of the helix. As a result, the cysteine residues are available for covalently attaching an organoarsenical component of a heterofinctional crosslinking reagent (e.g., a crosslinking reagent of formula I).

Formation of a covalent complex between the engineered protein and the crosslinking reagent (step (i)) can typically be accomplished by bringing the protein and reagent together in an aqueous or substantially aqueous solvent system, that is either neutral or buffered. Depending on the nature of the organoarsenical group present in the crosslinking reagent, the solvent system may require from 1% to 10% of a polar organic solvent such as DMF, DMSO, NMP or the like to provide a homogeneous mixture for covalent complex formation. Low concentrations of vicinal dithiols such as 1,2-ethanedithiol can be present in the solution to prevent covalent interaction between the organoarsenic group and cysteines in the recombinant proteins other than those present in the 4-cysteine-bearing helix. Additionally, complex formation can be carried out at temperatures of from about −15° C. to about 60° C., preferably from about 4° C. to about 37° C.

Following formation of the covalent association complex, the complex is illuminated with light of a suitable wavelength to activate the photocrosslinking group and form a covalent linkage between the photoactivatable group (Y, when a reagent of formula I is used) and the protein. Conditions for photoactivation will depend on the group Y. As in the methods described above, photoactivation can be accomplished using light having wavelengths of about 300–380 nm, more preferably about 315–380 nm and most preferably about 350–380 nm.

After a covalent linkage between the photoactivateable group and the protein has been formed, the organoarsenical group is released from the protein using a vicinal dithiol reagent such as EDT (about 5 mM), and the linking group $L^1$ is also cleaved by the appropriate treatment.

The resultant recombinant protein having an attached crosslinking reagent can then be labeled, attached to a probe, or attached to a solid support as described for the crosslinking group-modified proteins above.

In yet another aspect, the present invention provides a method for attaching a crosslinking reagent to a recombinant protein having an affinity tag, the method comprising:

(i) forming a non-covalent association complex between the recombinant protein affinity tag and a heterofunctional crosslinking reagent, wherein the heterofunctional crosslinking reagent comprises a presenting macromolecule portion specific for the affinity tag and attached to the remainder of the heterofanctional crosslinking reagent via a cleavable linking group, a photocrosslinking portion and a protected or unprotected chemical crosslinking portion that is unreactive to functional groups normally present on a protein;

(ii) illuminating the non-covalent association complex to form a covalent linkage between the recombinant protein and the photocrosslinking group of the heterofunctional crosslinking reagent; and (iii) releasing the presenting macromolecule portion from the affinity tag and from the heterofunctional crosslinking reagent to provide a recombinant protein having an attached reactive functional group.

In this aspect of the invention a protein having an affinity tag is provided wherein the protein is a recombinant protein and the affinity tag is engineered to provide a tag that can be recognized and bound by a heterofunctional crosslinking reagent having an affinity tag binder portion. The protein can generally be prepared using standard methods known to those of skill in the art.

The heterofunctional crosslinking reagents useful in this aspect of the invention are essentially those of formula III above. In addition to the affinity tags and protein tag binders described above, other tag/tag binder pairs are useful, including Tat/TAR, aptamer/substance P, DNA-binding/homeodomain, PDZ/PDZ-binding peptide, and calmodulin/calmodulin-binding peptide.

The conditions useful for each of steps (i), (ii) and (iii) are essentially the same as described for the related methods above. Thus, a non-covalent association complex can be formed between a protein having a suitable tag and a heterofunctional crosslinking reagent having a presenting macromolecule portion that is specific for the affinity tag by bringing each of the reactants together under mild, neutral conditions suitable for complex formation. Typically, an aqueous medium that is optionally buffered will be used and the components will be incubated at temperatures of about 0° C. to about 40° C., more preferably about 15° C. to about 25° C. A reaction time of about 6 hours or less is typically sufficient for complex formation, and reaction times of less than about 1 hour are common.

A covalent linkage between the crosslinking reagent and the non-covalent association complex can be formed by illuminating the complex with a suitable wavelength of light as described in methods above.

Finally, the presenting macromolecule portion can be released from the affinity tag and from the heterofunctional crosslinking reagent to provide a recombinant protein having an attached reactive functional group that is useful for incorporation of a probe or label into the protein, or for covalently attaching the protein to a solid support or surface.

In one group of embodiments, the recombinant protein is designed to include a specific RNA-binding peptide, such as the bovine immunodeficiency virus Tat sequence, which is 17 amino acids in length and binds to the TAR RNA (28 nucleotides in length) with a $K_D$ of about 1 nM. The TAR RNA (X in formula III) can be attached to the remainder of the heterofunctional crosslinking reagent so that binding to the Tat peptide would bring the photocrosslinking portion into close proximity with the recombinant protein. Photocrosslinking would then be performed as above. After the photocrosslinking step, the TAR RNA could be digested by treatment with RNAse. The three-dimensional structure of the Tat-TAR complex has been determined and can be used to guide placement of the remainder of the crosslinking reagent in the TAR RNA. The RNA is small enough to be chemically synthesized. Since the TAR RNA can be easily digested, it is not be necessary in this case to have a reversible bond ($L^1$ for reagents of formula III) between TAR and W. After digesting the TAR RNA, the Tat peptide can optionally be removed from the recombinant protein using a specific protease and an engineered protease cleavage site placed between Tat and the remaining portion of the recombinant protein. This embodiment will be particularly useful in cases where the photocrosslinking between Y and the recombinant protein occurs on the other side of the cleavage site from the Tat peptide. Thus, the arrangement of encoded units in the recombinant protein could be in the following order, from the N to C termini: protein of interest—protease cleavage site—Tat. In this case, the photocrosslinking would have to occur N-terminal to the cleavage site. Or, the elements of the construct could occur in the reverse order, and then the photocrosslinking would need to occur C-termninal to the cleavage site. The diagram in FIG. 4 shows the photocrosslinking occurring at or near the affinity tag sequence, but it could occur anywhere else in the recombinant protein, depending on the design of the constructs.

In another group of embodiments, the recombinant protein is designed to contain the "substance P" peptide sequence. This is an 11 amino acid long sequence that binds a known RNA aptamer with a $K_D$ of about 190 nM. The aptamer RNA (X in formula III) is derivatized with the remainder of the crosslinking reagent, so that binding to the substance P peptide would bring Y into close proximity with the recombinant protein. All other steps and considerations would be the same as described above. Other aptamer-peptide pairs could also be used.

In still other embodiments, the recombinant protein is designed so as to contain a specific DNA-binding peptide such as a homeodomain, which is about 60 amino acids in length and can bind a specific DNA sequence with a $K_D$ of about 1 nM. The DNA (X in formula III) is attached to the remainder of the crosslinking reagent, so that binding to the homeodomain peptide would bring Y into close proximity with the recombinant protein. All other steps are essentially the same as described above, except that DNAase rather than RNAase would be used to degrade the macromolecular component (X in formula III) of the crosslinking compound. The three-dimensional structure of several homeodomain-DNA complexes has been determined and are useful to guide placement of the remainder of the crosslinking reagent in the DNA. The DNA sequence is typically short enough (~15 base pairs) to be chemically synthesized. Other DNA-binding peptides, either natural or unnatural can also be used in place of homeodomains.

In still another group of embodiments, the recombinant protein will contain a peptide that interacts with a natural peptide-binding motif such as a PDZ domain. PDZ domains can interact with their cognate peptides with a $K_D$ of ~100 nM. The peptide-recognition sequences generally must reside at the C-terminus of the protein since the PDZ domain interacts with the carboxy terminus of target peptides. The PDZ domain would be derivatized with the remainder of the crosslinking group, so that binding to the recognition peptide would bring the photoactivatable portion into close proximity with the recombinant protein. The three-dimensional structures of PDZ domains, in complex with their cognate peptides, have been determined, and can be used to guide placement of the crosslinking group in the PDZ domain. The crosslinking reagent can be conjugated to the PDZ domain via a unique, introduced cysteine residue, for instance. In a second step, this modified PDZ domain would be incubated with the recombinant protein for the photocrosslinking process. After photocrosslinking, it may then be desirable to remove the PDZ domain. This could be accomplished by first breaking the PDZ-W bond, as described above and then competing the PDZ domain from the recombinant protein using excess free PDZ-binding peptide. Several other peptide-binding domains, such as the SH2 or SH3 domains, WW domains, etc. could be used in analogous experimental designs.

In yet another embodiment, the recombinant protein contains a calmodulin-binding-peptide (CBP). Calmodulin (X in formula III) can be incorporated into the crosslinking reagent so that binding to the CBP would bring the photoactivatable moiety into close proximity to the recombinant protein. The three-dimensional structures of calmodulin, in complex with CBPs, have been determined, and can be used to guide placement of the crosslinking reagent in calmodulin. One advantage of the calmodulin-peptide interaction is that it is dependent on the presence of calcium ions. Therefore, after the photocrosslinking reaction is complete, the non-covalent interaction could be inhibited by the addition of calcium-chelating agents such as EGTA.

For this and other embodiments wherein the crosslinker-presenting macromolecule is a protein, the site-specific attachment between this protein (X in Formula III) and the remainder of the crosslinking group could consist of a bond between a unique side-chain on the macromolecule, and a group that specifically reacts with this functional group. For example, the presenting macromolecule can contain a unique engineered cysteine residue that can be used to achieve a reversible disulfide bond to a thiol on the crosslinking compound.

Protein Arrays

In another aspect, the present invention provides protein arrays. Typically, the protein arrays comprise micrometer-scale, two-dimensional patterns of patches of proteins immobilized on an organic thinfilm coating on the surface of the substrate.

In one embodiment, the present invention provides an array of proteins which comprises a substrate, at least one organic thinfilm on some or all of the substrate surface, and a plurality of patches arranged in discrete, known regions on portions of the substrate surface covered by organic thinfilm, wherein each of said patches comprises a protein immobilized on the underlying organic thinfilm.

In most cases, the array will comprise at least about ten patches. In a preferred embodiment, the array comprises at least about 50 patches. In a particularly preferred embodiment the array comprises at least about 100 patches. In alternative preferred embodiments, the array of proteins may comprise more than $10^3$, $10^4$ or $10^5$ patches.

The area of surface of the substrate covered by each of the patches is preferably no more than about 0.25 mm$^2$. Preferably, the area of the substrate surface covered by each of the patches is between about 1 μm$^2$ and about 10,000 μm$^2$. In a particularly preferred embodiment, each patch covers an area of the substrate surface from about 100 μm$^2$ to about 2,500 μm$^2$. In an alternative embodiment, a patch on the array may cover an area of the substrate surface as small as about 2,500 nm$^2$, although patches of such small size are generally not necessary for the use of the array.

The patches of the array may be of any geometric shape. For instance, the patches may be rectangular or circular. The patches of the array may also be irregularly shaped.

The distance separating the patches of the array can vary. Preferably, the patches of the array are separated from neighboring patches by about 1 μm to about 500 μm. Typically, the distance separating the patches is roughly proportional to the diameter or side length of the patches on the array if the patches have dimensions greater than about 10 μm. If the patch size is smaller, then the distance separating the patches will typically be larger than the dimensions of the patch.

In a preferred embodiment of the array, the patches of the array are all contained within an area of about 1 cm² or less on the surface of the substrate. In one preferred embodiment of the array, therefore, the array comprises 100 or more patches within a total area of about 1 cm² or less on the surface of the substrate. Alternatively, a particularly preferred array comprises $10^3$ or more patches within a total area of about 1 cm² or less. A preferred array may even optionally comprise $10^4$ or $10^5$ or more patches within an area of about 1 cm² or less on the surface of the substrate. In other embodiments of the invention, all of the patches of the array are contained within an area of about 1 m² or less on the surface of the substrate.

Typically, only one type of protein is immobilized on each patch of the array. In a preferred embodiment of the array, the protein immobilized on one patch differs from the protein immobilized on a second patch of the same array. In such an embodiment, a plurality of different proteins are present on separate patches of the array. Typically the array comprises at least about ten different proteins. Preferably, the array comprises at least about 50 different proteins. More preferably, the array comprises at least about 100 different proteins. Alternative preferred arrays comprise more than about $10^3$ different proteins or more than about $10^4$ different proteins. The array may even optionally comprise more than about $10^5$ different proteins.

In one embodiment of the array, each of the patches of the array comprises a different protein. For instance, an array comprising about 100 patches could comprise about 100 different proteins. Likewise, an array of about 10,000 patches could comprise about 10,000 different proteins. In an alternative embodiment, however, each different protein is immobilized on more than one separate patch on the array. For instance, each different protein may optionally be present on two to six different patches. An array of the invention, therefore, may comprise about three-thousand protein patches, but only comprise about one thousand different proteins since each different protein is present on three different patches.

In another embodiment of the present invention, although the protein of one patch is different from that of another, the proteins are related. In a preferred embodiment, the two different proteins are members of the same protein family. The different proteins on the invention array may be either functionally related or just suspected of being functionally related. In another embodiment of the invention array, however, the function of the immobilized proteins may be unknown. In this case, the different proteins on the different patches of the array share a similarity in structure or sequence or are simply suspected of sharing a similarity in structure or sequence. Alternatively, the immobilized proteins may be just fragments of different members of a protein family.

The proteins immobilized on the array of the invention may be members of a protein family such as a receptor family (examples: growth factor receptors, catecholamine receptors, amino acid derivative receptors, cytokine receptors, lectins), ligand family (examples: cytokines, serpins), enzyme family (examples: proteases, kinases, phosphatases, ras-like GTPases, hydrolases), and transcription factors (examples: steroid hormone receptors, heat-shock transcription factors, zinc-finger proteins, leucine-zipper proteins, homeodomain proteins). In one embodiment, the different immobilized proteins are all HIV proteases or hepatitis C virus (HCV) proteases. In other embodiments of the invention, the immobilized proteins on the patches of the array are all hormone receptors, neurotransmitter receptors, extracellular matrix receptors, antibodies, DNA-binding proteins, intracellular signal transduction modulators and effectors, apoptosis-related factors, DNA synthesis factors, DNA repair factors, DNA recombination factors, or cell-surface antigens.

In a preferred embodiment, the protein immobilized on each patch is an antibody or antibody fragment. The antibodies or antibody fragments of the array may optionally be single-chain Fvs, Fab fragments, Fab' fragments, F(ab')2 fragments, Fv fragments, dsFvs diabodies, Fd fragments, full-length, antigen-specific polyclonal antibodies, or full-length monoclonal antibodies. In a preferred embodiment, the immobilized proteins on the patches of the array are monoclonal antibodies, Fab fragments or single-chain Fvs.

In another preferred embodiment of the invention, the proteins immobilized to each patch of the array are protein-protein tag combinations.

In an alternative embodiment of the invention array, the proteins on different patches are identical.

Biosensors, micromachined devices, and diagnostic devices that comprise the protein arrays of the invention are also contemplated by the present invention.

The physical structure of the protein arrays will typically comprise a substrate and, optionally, a coating or organic thinfilm or both.

The substrate of the array may be either organic or inorganic, biological or non-biological, or any combination of these materials. In one embodiment, the substrate is transparent or translucent. The portion of the surface of the substrate on which the patches reside is preferably flat and firm or semi-firm. However, the array of the present invention need not necessarily be flat or entirely two-dimensional. Significant topological features may be present on the surface of the substrate surrounding the patches, between the patches or beneath the patches. For instance, walls or other barriers may separate the patches of the array.

Numerous materials are suitable for use as a substrate in the array embodiment of the invention. For instance, the substrate of the invention array can comprise a material selected from a group consisting of silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for substrates of the array. In addition, many ceramics and polymers may also be used as substrates. Polymers which may be used as substrates include, but are not limited to, the following: polystyrene; poly(tetra)fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyatkenesulfone (PAS); polypropylene; polyethylene; polyhydroxyethylmethacrylate (HEMA); polydimethylsiloxane; polyacrylamide; polyimide; and block-copolymers. Preferred substrates for the array include silicon, silica, glass, and polymers. The substrate on which the patches reside may also be a combination of any of the aforementioned substrate materials.

An array of the present invention may optionally further comprise a coating between the substrate and organic thinfilm on the array. This coating may either be formed on the substrate or applied to the substrate. The substrate can be modified with a coating by using thin-film technology based, for example, on physical vapor deposition (PVD), thermal processing, or plasma-enhanced chemical vapor deposition (PECVD). Alternatively, plasma exposure can be used to directly activate or alter the substrate and create a coating. For instance, plasma etch procedures can be used to oxidize a polymeric surface (i.e., polystyrene or polyethylene to expose polar functionalities such as hydroxyls, carboxylic acids, aldehydes and the like).

The coating is optionally a metal film. Possible metal films include aluminum, chromium, titanium, tantalum, nickel, stainless steel, zinc, lead, iron, copper, magnesium, manganese, cadmium, tungsten, cobalt, and alloys or oxides thereof. In a preferred embodiment, the metal film is a noble metal film. Noble metals that may be used for a coating include, but are not limited to, gold, platinum, silver, and copper. In an especially preferred embodiment, the coating comprises gold or a gold alloy. Electron-beam evaporation may be used to provide a thin coating of gold on the surface of the substrate. In a preferred embodiment, the metal film is from about 50 nm to about 500 nm in thickness. In an alternative embodiment, the metal film is from about 1 nm to about 1 µm in thickness.

In alternative embodiments, the coating comprises a composition selected from the group consisting of silicon, silicon oxide, titania, tantalum oxide, silicon nitride, silicon hydride, indium tin oxide, magnesium oxide, alumina, glass, hydroxylated surfaces, and polymers.

In one embodiment of the invention array, the surface of the coating is atomically flat. In this embodiment, the mean roughness of the surface of the coating is less than about 5 angstroms for areas of at least 25 µm$^2$. In a preferred embodiment, the mean roughness of the surface of the coating is less than about 3 angstroms for areas of at least 25 µm$^2$. The ultraflat coating can optionally be a template-stripped surface as described in Heguer et al., *Surface Science*, 1993, 291:39–46 and Wagner et al., *Langmuir*, 1995, 11:3867–3875, both of which are incorporated herein by reference.

It is contemplated that the coatings of many arrays will require the addition of at least one adhesion layer between said coating and the substrate. Typically, the adhesion layer will be at least 6 angstroms thick and may be much thicker. For instance, a layer of titanium or chromium may be desirable between a silicon wafer and a gold coating. In an alternative embodiment, an epoxy glue such as Epo-tek 377®, Epo-tek 301-2®, (Epoxy Technology Inc., Billerica, Mass.) may be preferred to aid adherence of the coating to the substrate. Determinations as to what material should be used for the adhesion layer would be obvious to one skilled in the art once materials are chosen for both the substrate and coating. In other embodiments, additional adhesion mediators or interlayers may be necessary to improve the optical properties of the array, for instance, in waveguides for detection purposes.

Deposition or formation of the coating (if present) on the substrate is performed prior to the formation of the organic thinfilm thereon. Several different types of coating may be combined on the surface. The coating may cover the whole surface of the substrate or only parts of it. The pattern of the coating may or may not be identical to the pattern of organic thinfilms used to immobilize the proteins. In one embodiment of the invention, the coating covers the substrate surface only at the site of the patches of the immobilized protein(s). Techniques useful for the formation of coated patches on the surface of the substrate which are organic thinfilm-compatible are well known to those of ordinary skill in the art. For instance, the patches of coatings on the substrate may optionally be fabricated by photolithography, micromolding (PCT Publication WO 96/29629), wet chemical or dry etching, or any combination of these.

The organic thinfilm on which each of the patches of proteins is immobilized forms a layer either on the substrate itself or on a coating covering the substrate. The organic thinfilm on which the proteins of the patches are immobilized is preferably less than about 20 nm thick. In some embodiments of the invention, the organic thinfilm of each of the patches may be less than about 10 nm thick.

A variety of different organic thinfilms are suitable for use in the present invention. Methods for the formation of organic thinfilms include in situ growth from the surface, deposition by physisorption, spin-coating, chemisorption, self-assembly, or plasma-initiated polymerization from gas phase. For instance, a hydrogel composed of a material such as dextran can serve as a suitable organic thinfilm on the patches of the array. In one preferred embodiment of the invention, the organic thinfilm is a lipid bilayer. In another preferred embodiment, the organic thinfilm of each of the patches of the array is a monolayer. A monolayer of polyarginine or polylysine adsorbed on a negatively charged substrate or coating is one option for the organic thinfilm. Another option is a disordered monolayer of tethered polymer chains. In a particularly preferred embodiment, the organic thinfilm is a self-assembled monolayer. A monolayer of polylysine is one option for the organic thinfilm. See Wagner, et al. U.S. patent application Ser. Nos. 09/353,215 and 09/353,555, both of which are herein incorporated by reference in their entirety for all purposes including methods and devices for displaying compounds in an array.

In preferred embodiments, the coating, or the substrate itself if no coating is present, should be compatible with the chemical or physical adsorption of the organic thinfilm on its surface. For instance, if the patches comprise a coating between the substrate and a monolayer of molecules of the formula I, then it is understood that the coating should be composed of a material capable of binding the heterofunctional crosslinking group of formula I. If no such coating is present, then it is understood that the substrate must be composed of a material which can covalently bind the heterofunctional crosslinking group.

In a preferred embodiment of the invention, the regions of the substrate surface, or coating surface, which separate the patches of proteins are free of organic thinfilm. In an alternative embodiment, the organic thinfilm extends beyond the area of the substrate surface, or coating surface if present, covered by the protein patches. For instance, optionally, the entire surface of the array may be covered by an organic thinfilm on which the plurality of spatially distinct patches of proteins reside. An organic thinfilm which covers the entire surface of the array may be homogeneous or may optionally comprise patches of differing exposed functionalities useful in the immobilization of patches of different proteins. In still another alternative embodiment, the regions of the substrate surface, or coating surface if a coating is present, between the patches of proteins are covered by an organic thinfilm, but an organic thinfilm of a different type than that of the patches of proteins. For instance, the surfaces between the patches of proteins may be coated with an organic thinfllm characterized by low non-specific binding properties for proteins and other analytes.

A variety of techniques may be used to generate patches of organic thinfilm on the surface of the substrate or on the surface of a coating on the substrate. These techniques are well known to those skilled in the art and will vary depending upon the nature of the organic thinfilm, the substrate, and the coating if present. The techniques will also vary depending on the structure of the underlying substrate and the pattern of any coating present on the substrate. For instance, patches of a coating which is highly reactive with an organic thinfilm may have already been produced on the substrate surface. Arrays of patches of organic thinfilm can optionally be created by microfluidics printing, microstamping (U.S. Pat. Nos. 5,512,131 and 5,731,152), or microcontact printing (p.CP) (PCT Publication WO 96/29629). Subsequent immobilization of proteins to the reactive monolayer patches results in two-dimensional arrays of the agents. Inkjet printer heads provide another option for patterning monolayer molecules, or components thereof, or other organic thinfilm components to nanometer or micrometer scale sites on the surface of the substrate or coating (Lemmo et al, *Anal Chem.*, 1997, 69:543–55 1; U.S. Pat. Nos. 5,843,767 and 5,837,860). In some cases, commercially available arrayers based on capillary dispensing (for instance, OmniGrid™ from Genemachines, Inc, San Carlos, Calif., and High-Throughput Microarrayer from Intelligent Bio-Instruments, Cambridge, Mass.) may also be of use in directing components of organic thinfilms to spatially distinct regions of the array.

Diffusion boundaries between the patches of proteins immobilized on organic thinfilms such as self-assembled monolayers may be integrated as topographic patterns (physical barriers) or surface functionalities with orthogonal wetting behavior (chemical barriers). For instance, walls of substrate material or photoresist may be used to separate some of the patches from some of the others or all of the patches from each other. Alternatively, non-bioreactive organic thinfilms, such as monolayers, with different wettability may be used to separate patches from one another.

In a preferred embodiment of the invention, each of the patches of proteins comprises proteins attached to the surface using a heterofunctional crosslinking group of formula I, as previously defined.

A variety of chemical moieties may function as monolayer molecules which can be attached to the heterofunctional crosslinking group (Z) in the arrays described herein. However, three major classes of monolayer formation are preferably used to expose high densities of reactive omega-functionalities on the patches of the array: (i) alkylsiloxane monolayers ("silanes") on hydroxylated and non-hydroxylated surfaces (as taught in, for example, U.S. Pat. No. 5,405,766, PCT Publication WO 96/38726, U.S. Pat. No. 5,412,087, and U.S. Pat. No. 5,688,642); (ii) alkyl-thiol/dialkyldisulfide monolayers on noble metals (preferably Au(111)) (as, for example, described in Allara et al, U.S. Pat. No. 4,690,715; Bamdad et al., U.S. Pat. No. 5,620,850; Wagner et al., *Biophysical Journal*, 1996, 70:2052–2066); and (iii) alkyl monolayer formation on oxide-free passivated silicon (as taught in, for example, Linford et al., *J. Am. Chem. Soc.*, 1995, 117:3145–3155, Waguer et al., *Journal of Structural Biology*, 1997, 119:189–201, U.S. Pat. No. 5,429, 708). One of ordinary skill in the art, however, will recognize that many possible moieties may be used and are described in Ulman, An Introduction to *Ultrathin Organic Films: From Langmuir-Blodgett to Self Assembly*, Academic press (1991).

If the patches of the invention array comprise a self-assembled monolayer of molecule, then a spacer may optionally be used which comprises a linear or branched hydrocarbon chain from about 1 to about 400 carbons long. The hydrocarbon chain may comprise an alkyl, aryl, alkenyl, alkynyl, cycloalkyl, alkaryl, aralkyl group, or any combination thereof. Alternatively, the spacer may comprise a linear or branched hydrocarbon chain from about 2 to about 400 carbons long and be interrupted by at least one heteroatom or hetero group. The interrupting hetero groups can include —O—, —CONH—, —CONHCO—, —NH—, —CSNH—, —CO—, —CS—, —S—, —SO—, —(OCH$_2$CH$_2$)$_n$— (where n=1–20), —(CF$_2$)$_n$— (where n=1–22), and the like.

The monolayer molecule may be chosen as any group which affords chemisorption or physisorption of the monolayer onto the surface of the substrate (or the coating, if present). When the substrate or coating is a metal or metal alloy, the monolayer molecule, at least prior to incorporation into the monolayer, can in one embodiment be chosen to be an asymmetrical or symmretrical disulfide, sulfide, diselenide, selenide, thiol, isonitrile, selenol, a trivalent phosphorus compound, isothiocyanate, isocyanate, xanthanate, thiocarbamate, a phosphine, an amine, thio acid or a dithio acid. This embodiment is especially preferred when a coating or substrate is used that is a noble metal such as gold, silver, or platinum.

If the substrate of the array is a material such as silicon, silicon oxide, indium tin oxide, magnesium oxide, alumina, quartz, glass, or silica, then the array of one embodiment of the invention comprises a monolayer molecule that, prior to incorporation into a monolayer, is a monohalosilane, dihalosilane, trihalosilane, trialkoxysilane, dialkoxysilane, or a monoalkoxysilane. Among these silanes, trichlorosilane and trialkoxysilane are particularly preferred.

In a preferred embodiment of the invention, the substrate is selected from the group consisting of silicon, silicon dioxide, indium tin oxide, alumina, glass, and titania; and X, prior to incorporation into said monolayer, is selected from the group consisting of a monohalosilane, dihalosilane, trihalosilane, trichlorosilane, trialkoxysilane, dialkoxysilane, monoalkoxysilane, carboxylic acids, and phosphates.

If the substrate used in the invention is a polymer, then in many cases a coating on the substrate such as a copper coating will be included in the array. An appropriate fuinctional group for the coating would then be chosen for use in the array. In an alternative embodiment comprising a polymer substrate, the surface of the polymer may be plasma-modified to expose desirable surface functionalities for monolayer formation. For instance, EP 780423 describes the use of a monolayer molecule that has an alkene functionality on a plasma exposed surface. Still another possibility for the invention array comprised of a polymer is that the surface of the polymer on which the monolayer is formed is functionalized by copolymerization of appropriately functionalized precursor molecules.

In another embodiment, prior to incorporation into the monolayer, the monolayer molecule can comprise a free-radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyano compounds and isonitrile compounds can be used when rendered reactive in the presence of ultraviolet, infrared, visible, or microwave radiation.

In alternative embodiments, the monolayer molecule, prior to incorporation into the monolayer, will comprise a hydroxyl, carboxyl, vinyl, sulfonyl, phosphoryl, silicon hydride, or an amino group.

In another aspect, the present invention provides a method for attaching an altering member to a protein or polypeptide, the method comprising:

a) contacting the polypeptide or protein with an altering member to form a chemically specific, non-covalent complex having a polypeptide or protein component and an altering component; and b) providing conditions sufficient to form a covalent bond between the polypeptide or protein component and the altering component;

wherein the functional groups taking part in complex formation and in covalent bond formation are different and step b) is subsequent to step a), and with the proviso that when the polypeptide or protein is an enzyme, the altering member is other than an active-site directed substrate or modified substrate.

These methods take advantage of functional groups that can be involved in specific recognition as well as functional groups that are considered unreactive, until exposed to an external stimulus or conditions that render the second functional group reactive in a covalent bond forming sense.

Accordingly, the altering members used herein are those components that have both a specific, non-covalent recognition group and a covalent attaching group. Examples of specific, non-covalent recognition groups include those groups described above (e.g., leucine zippers, organoarsenical groups, see also U.S. Ser. No. 60/235,955, filed Sep. 26, 2000) and groups (e.g., protein tag binders) provided in related and co-pending application Ser. No. 60/192,640, filed Mar. 27, 2000, each application being incorporated herein by reference. Other non-limiting examples of specific, non-covalent recognition groups include metal chelating agents that are specific for a metal ion associated with a particular polypeptide.

The covalent attaching group is preferably a functional group that is unreactive until activated by a stimulus, preferably an external stimulus such as light, heat or an additional chemical reagent. For example, suitable covalent attaching groups include those that generate a reactive radical species on exposure to a suitable light source (e.g., benzophenone groups as described above). Other non-limiting examples of covalent attaching groups include reactive functional groups (e.g., OH, $NH_2$ or SH) that are masked by a protecting group that can be selectively removed either by light, heat or a specific chemical reagent.

Thus, in its broadest sense, this aspect of the invention provides methods of attaching essentially any label, support, ligand, or other component (or altering species) to a polypeptide or protein. The altering species is brought into a non-covalent association with the polypeptide or protein that is specific for a particular site on the polypeptide or protein. In response to an external stimulus, a covalent bond is then formed between the polypeptide or protein and a reactive functional group present on the altering species.

EXAMPLES

Example 1

This example illustrates the preparation of a heterofunctional crosslinking reagent specific for 6× His-tagged proteins (see Scheme 1).

As shown in Scheme 1, a diaminoalkane (e.g., 1,7-diaminoheptane, 1,11-diaminoundecane or 1,13-diaminotridecane) i can be treated with di-t-butylcarbonate to provide the mono-protected amine, ii. Coupling of ii with the activated ester iv (produced from 4-benzoylbenzoic acid and N-hydroxysuccinimide (NHS) and EDC) provides a photoactivatable group with an attached linking group (v). Removal of the Boc protecting group from v using trifluoroacetic acid and subsequent coupling of Fmoc-Cys(SStBu)-OPfp to the liberated amino group provides vi. Removal of the Fmoc group from vi under standard conditions provides vii. The free amine can then be attached to a linking group (here, —$C(O)CH_2CH_2CO_2H$) using known conditions to provide viii. Activation of the carboxylic acid group of viii using NHS and EDC provides ix, which can be converted to the target heterofunctional crosslinking group upon treatment with the trisodium salt $ix_a$.

SCHEME 1

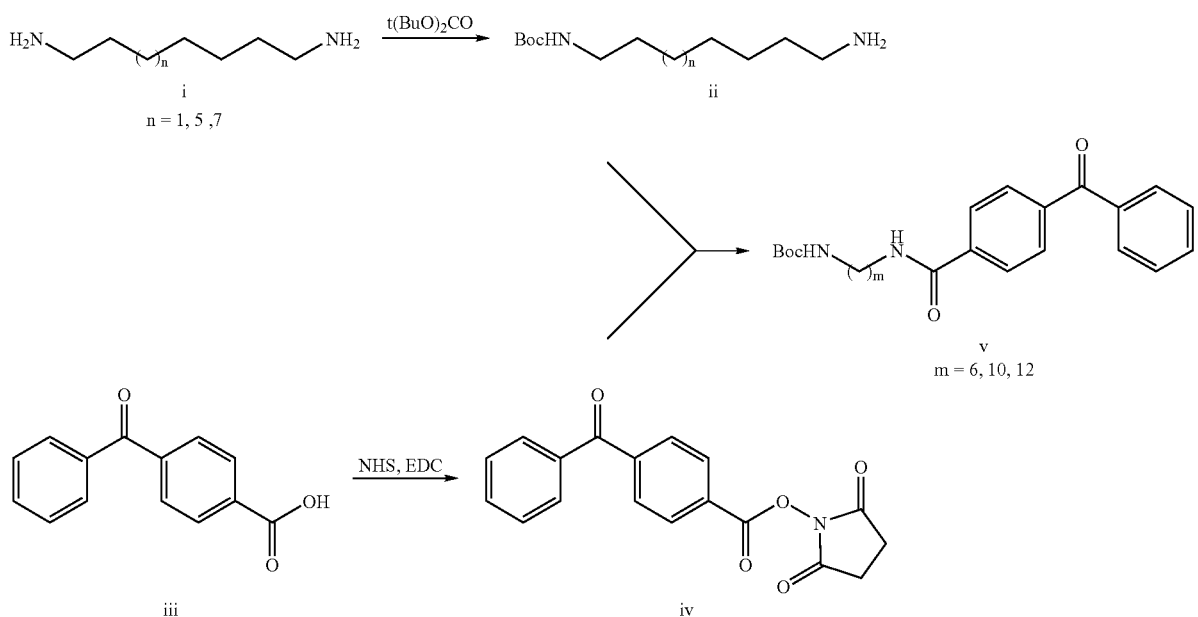

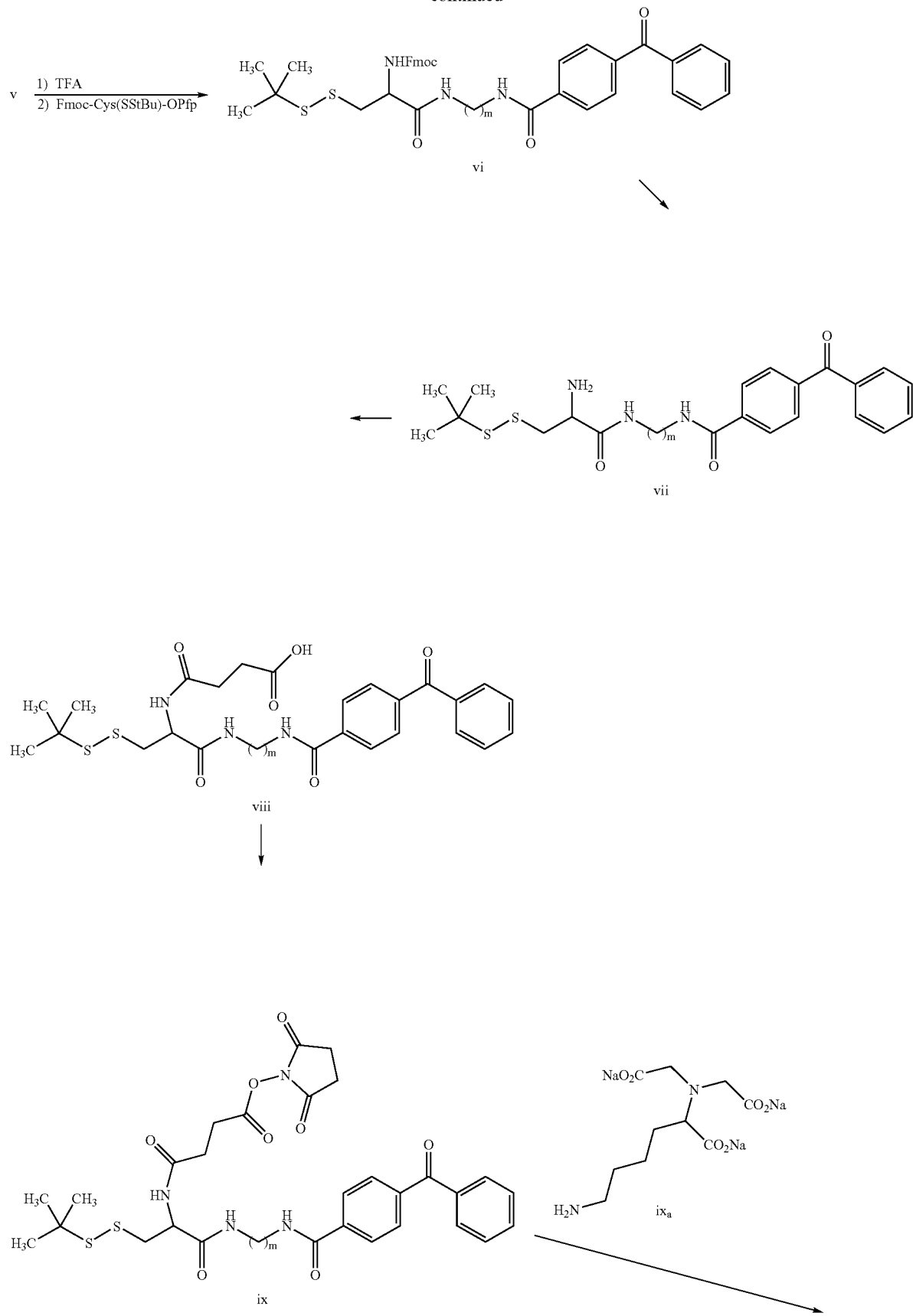

-continued

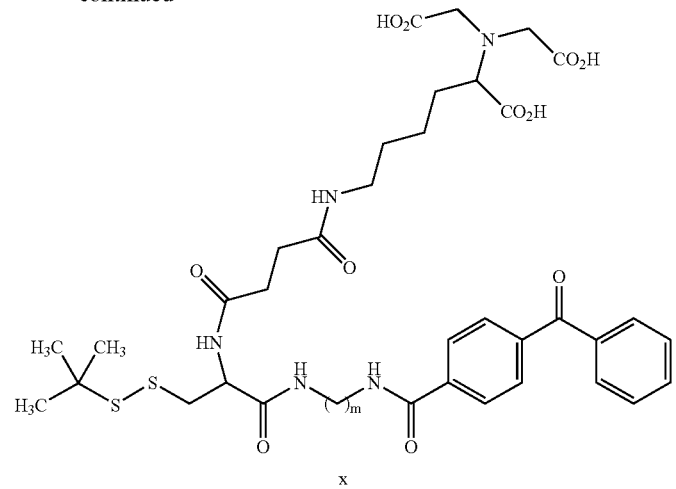

x

Example 2

This example illustrates structures for heterofunctional crosslinking groups of the present invention, including crosslinking group x. In particular, compound x is a crosslinking group having an amino acid core component with an attached (via alkylene linker) photoactivatable group and an attached (via substituted heteroalkylene linker) nitrilotriacetic acid tag binder. The functional group Z is depicted as a protected cysteine sidechain thiol. Crosslinkers xi and xii are similarly developed based on a lysine scaffold and a glutamic acid scaffold, respectively.

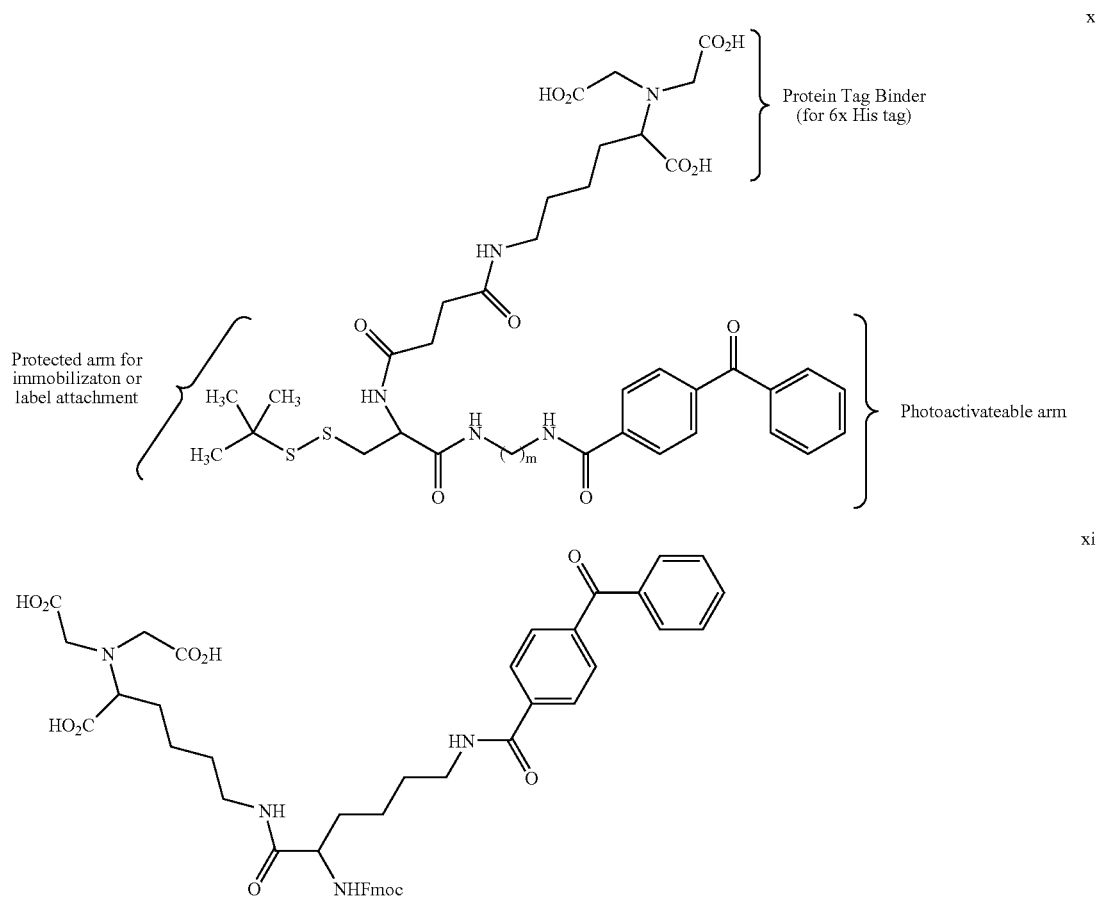

-continued
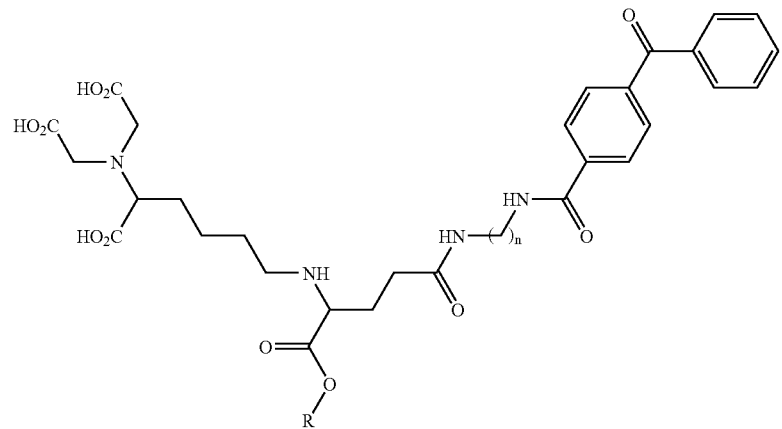
xii
Example 3
This example illustrates the preparation of a crosslinking group-label conjugate as illustrated in Scheme 2.
SCHEME 2
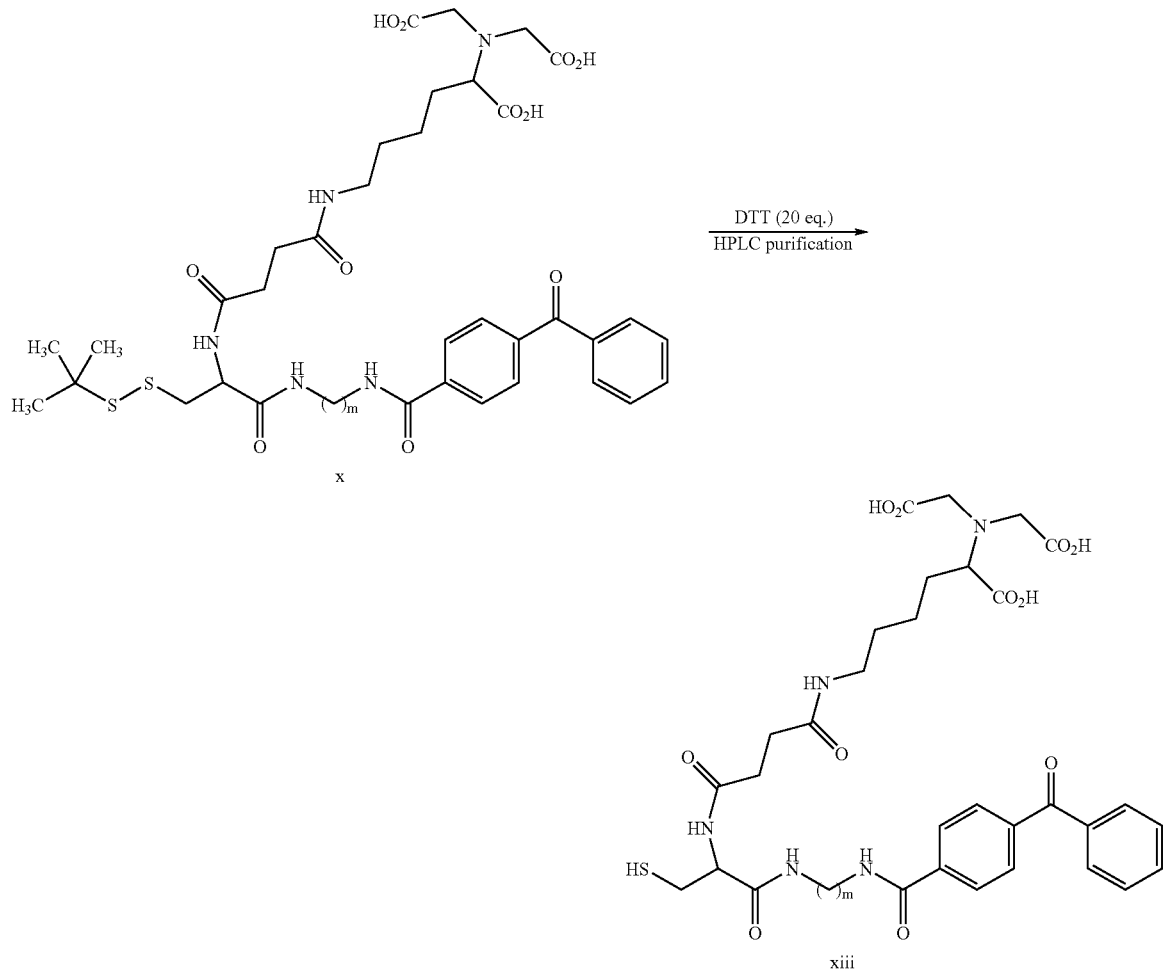

-continued

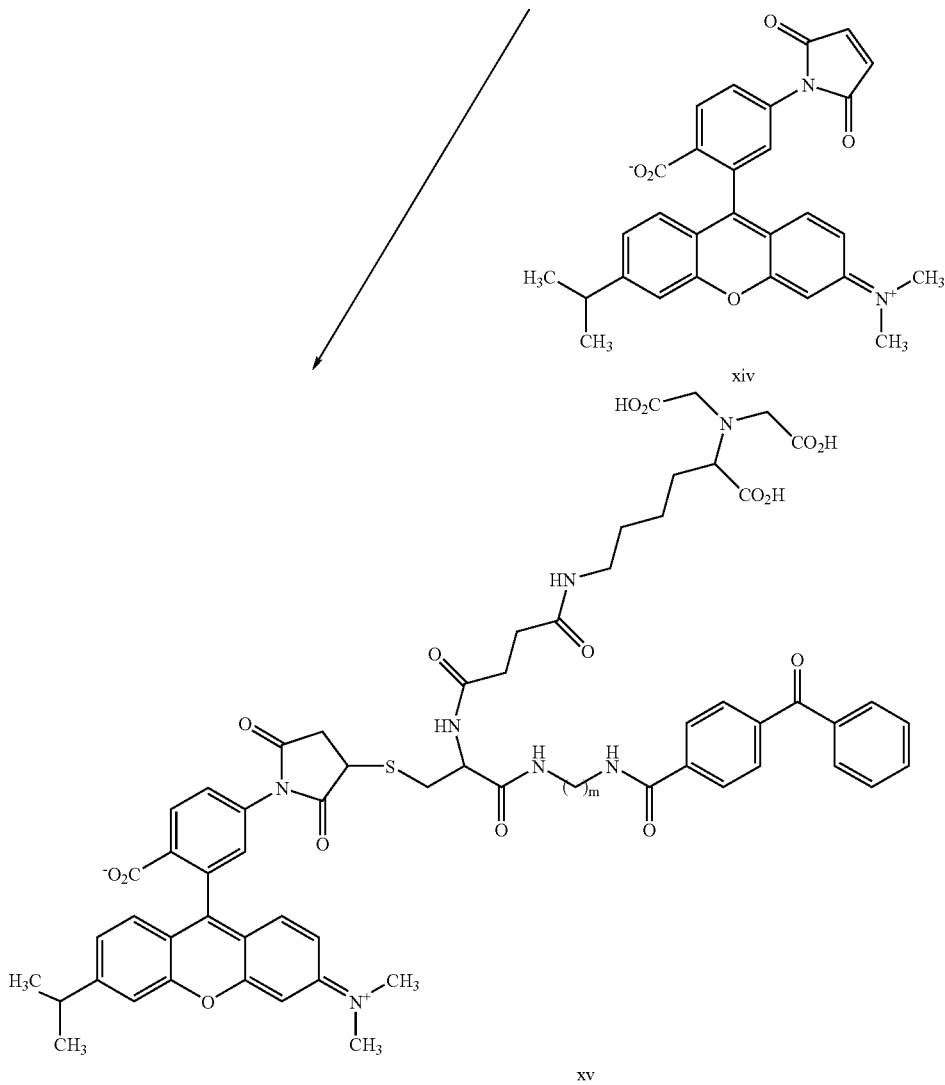

xv

As shown in Scheme 2, a heterofunctional crosslinking group x can be deprotected using dithiothreitol (DTT) and purified by HPLC to provide xiii. Treatment xiii with a suitable label (e.g., xiv) provides the conjugate xv.

Example 4

This example illustrates the preparation of a linking group having one component of a leucine zipper and the incorporation of a second component of a leucine zipper into a targeted protein.

Leucine zipper helices can be constructed as described in Wendt, et al., *Biochemistry* 36:204–213 (1996), having the following sequences:
Helix A (acidic): EYQALEKEVAQLEAENNALEKEVA-QLEHEG
Helix B (basic): EYQALKKKVAQLKAKNNALKKKVA-QLKHKG
This pair of helices is based on the homodimeric GCN4 leucine zipper, but differs by replacing several amino acids with either glutamic acid (to generate the acidic Helix A) or lysine (to generate the basic Helix B). The generated pair of peptides can interact with high affinity to form a parallel heterodimer having a dissociation constant of about 6 nM, with no observable tendency to form homodimers or antiparallel heterodimers. Because each of these peptides is highly charged, they are very soluble in aqueous and polar environments and are in a disordered conformation when isolated from each other.

The strong interaction between the helices can be used for the immobilization of proteins on a surface by fusing the first peptide sequence to a protein terminus and allowing this first peptide sequence to bind to the second peptide sequence. The second peptide sequence in this example is immobilized on a surface prior to being introduced to the first sequence. Alternatively, binding of the two helical peptides can be pursued first, with the immobilization to the surface through the Z group occurring second.

Helix A

The acidic helix A can synthesized by solid-phase peptide synthesis using an optimized Boc-chemistry protocol (Schnoelzer et al., *Int. J. Peptide Protein Res.*, 40:180–193 (1992)) with the following modified sequence:

EYQALEKEVAQLEAENNALEKEVAQLEHYGGSGZ

Y is an amino acid containing a photoactive crosslinking moiety that can be used to covalently link the two helices together after they have non-covalently bound to each other. An example of Y is p-Benzoyl-L-phenylalanine which has been incorporated into other peptides for crosslinking studies using Boc-chemistry (e.g. Girault et al., *Eur. J. Biochem.*, 240:215–222 (1996)).

The group Z is the compoment that will be used for surface immobilization of the helix and/or protein. A cysteine can be placed at that position for the immobilization of the peptide on a maleimide surfaces (Xiao et al., *Langmuir*, 14:5507–5516 (1998)).

Alternatively, the group Z can be an unnatural group like a triarylphosphine or a ketone that reacts specifically with an azide or hydrazine surface, respectively.

The following scheme depicts the basic structure of the helix that will be immobilized onto the surface.

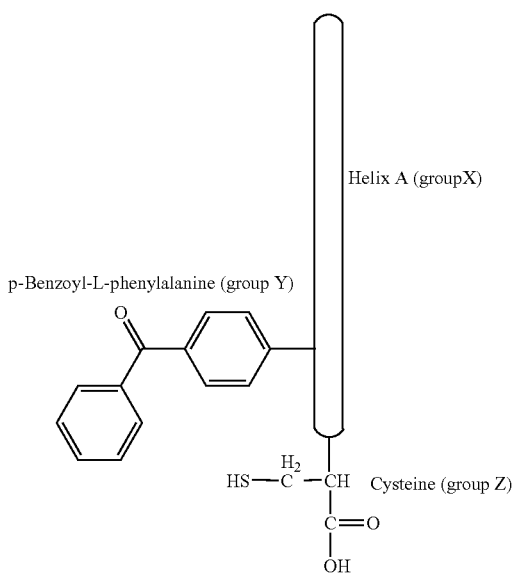

This modified helix A can then be immobilized onto a surface for the subsequent immobilization of a target protein-helix B fusion.

Helix B

The basic helix B can be incorporated at the C-terminus of the target protein to be immobilized on the surface. The incorporation can be carried out by cloning the sequence of the helix at the 3' end of the target protein sequence with standard recombinant DNA-technologies (Sambrook et al., Molecular Cloning, Cold Spring Harbor Laboratory Press, 1989).

The protein can be purified by the introduction of a His-Tag between the protein and the helix sequence which can be used for the purification by Ni-NTA-chromatography (Janknecht et al., *PNAS*, 88:8972–8976 (1991)).

The target protein-helix B fusion can then be covalently linked onto the surface by a specific binding of helix B to helix A on the surface followed by a subsequent crosslinking reaction with the benzophenone moiety upon irradiation with UV light (Girault et al., *Eur. J. Biochem.*, 240:215–222 (1996); and Weber & Beck-Sickinger, *J. Peptide Res.*, 49:375–383 (1997)).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A heterofunctional crosslinking reagent having the formula:

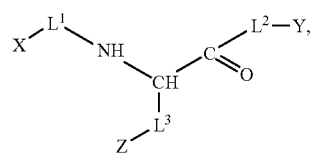

wherein
$L^1$ and $L^2$ are each independently selected from the group consisting of a bond, a substituted or unsubstituted ($C_2$–$C_{24}$) alkylene group, a substituted or unsubstituted ($C_2$–$C_{24}$) heteroallcylene group, a polyethyleneglycol group, a polyalcohol group, a polyamine group, a poiyester group and a polyphosphodiester group;
-$L^3$-Z is an optionally protected amino acid side chain having a pendant reactive group, wherein said amino acid is selected from the group consisting of lysine, cysteine, serine, aspartic acid, glutamic acid, and threonine;
X is a non-covalent protein tag binder that specifically binds to a protein tag portion of a protein; and
Y is a photoactivatable covalent crosslinking group adapted to covalently link the heterofunctional crosslinking reagent at or adjacent to said protein tag, said photoactivatable covalent crosslinking group is a member selected from the group consisting of aryl ketones, azides, diazo compounds, diazirenes, and ketenes.

2. A heteroflinctional crosslinking reagent of claim 1, wherein $L^1$ is a cleavable linking group.

3. A heterofunctional crosslinking reagent of claim 1, wherein X is selected from the group consisting of metal chelating groups, peptides, an organoarsenical moiety and small molecule ligands or inhibitors.

4. A protein conjugate comprising a protein and a heterofunctional crosslinking reagent, said conjugate having the formula:

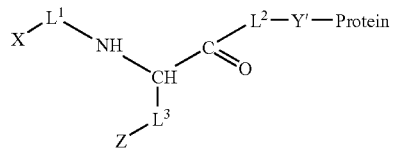

wherein
$L^1$ and $L^2$ are each independently selected from the group consisting of a bond, a substituted or unsubstituted ($C_2$–$C_{24}$) alkylene group, a substituted or unsubstituted ($C_2$–$C_{24}$) heteroalkylene group, a polyethyleneglycol group, a polyalcohol group, a polyamine group, a polyester group and a polyphosphodiester group;

-L³-Z is an optionally protected amino acid side chain having a pendant reactive group, wherein said amino acid is selected from the group consisting of lysine, cysteine, serine, aspartic acid, glutamic acid, and threonine;

X is a non-covalent protein tag binder that specifically binds to a protein tag portion of said protein; and Y' is the residue of a photoactivatable covalent crosslinking group after formation of a covalent linkage to said protein, said photoactivatable covalent crosslinking group covalently attached at or adjacent to said protein tag portion of said protein, said photoactivatable covalent crosslinking group is a member selected from the group consisting of aryl ketones, azides, diazo compounds, diazirenes, and ketenes.

5. A heterofunctional crosslinking reagent of claim 1, wherein X is an antibody or antibody fragment.

* * * * *